(12) United States Patent
Kumagai et al.

(10) Patent No.: US 7,635,475 B2
(45) Date of Patent: Dec. 22, 2009

(54) DIABODY-TYPE BISPECIFIC ANTIBODY

(75) Inventors: Izumi Kumagai, Miyagi (JP); Toshio Kudo, Miyagi (JP); Kouhei Tsumoto, Miyagi (JP); Ryutaro Asano, Miyagi (JP)

(73) Assignee: Tohoku Techno Arch Co., Ltd., Sendai-Shi (JP)

( * ) Notice: Subject to any disclaimer, the term of this patent is extended or adjusted under 35 U.S.C. 154(b) by 309 days.

(21) Appl. No.: 10/642,284

(22) Filed: Aug. 18, 2003

(65) Prior Publication Data
US 2006/0210564 A1 Sep. 21, 2006

(30) Foreign Application Priority Data
Feb. 17, 2003 (JP) .............................. 2003-038643

(51) Int. Cl.
A61K 39/395 (2006.01)
C12P 21/08 (2006.01)
(52) U.S. Cl. .............. 424/136.1; 424/143.1; 424/144.1; 424/155.1; 530/387.1; 530/387.3; 530/387.7; 530/388.1; 530/388.22; 530/388.75; 530/388.8; 530/388.85
(58) Field of Classification Search .............. 424/135.1, 424/136.1, 136.11, 143.1, 144.1, 155.1; 530/387.1, 530/387.3, 387.7, 388.1, 388.22, 288.75, 530/388.8, 388.85
See application file for complete search history.

(56) References Cited

U.S. PATENT DOCUMENTS

| 4,943,533 A | * | 7/1990 | Mendelsohn et al. ... 530/388.22 |
| 5,922,845 A | * | 7/1999 | Deo et al. ................. 530/387.3 |
| 6,407,213 B1 | * | 6/2002 | Carter et al. ............. 530/387.3 |

FOREIGN PATENT DOCUMENTS

| WO | WO-94/28027 A1 | 12/1994 |
| WO | WO-95/16037 A1 | 6/1995 |
| WO | WO 00/23087 A1 | 4/2000 |
| WO | WO 02/06486 A1 | 1/2002 |

OTHER PUBLICATIONS

Kipriyanov, G. et al., Protein Engineering, 10(4): 445-453, 1997.*
Rudikoff, Proc. Natl. Acad. Sci. USA, 79: 1979, 1982.*
Clackson, T. et al. Nature, 352: 624-628, 1991.*
Renard, I., et al. American Journal of Pathology, 160(1): 113-122, Jan. 2002).*
Krebber, A. et al. Journal of Immunological Methods, 201: 35-55, 1997.*
Gussow, D. and Seemann, G. Methods in Enzymology, 203: 99-121, 1991.*
Hiroki Hayashi et al., Abstract #2125, 75th Annual Congress of The Japanese Biochemical Society, 74(8): Aug. 25, 2002; cited in the IDS; English translation.*
Gill, G.N. et al., The Journal of Biological Chemistry, 259(12): 7755-7760, 1984.*
Wu, H. et al., J. Mol. Biol., 294: 151-162, 1999.*
Asano, R. et al., Abstract 3P-214, 75th Annual Congress of The Japanese Biochemical Society, 74(8): Aug. 25, 2002; English translation of document cited in IDS.*
Hayashi, Hiroki, et al., The 61st General Meeting of Japanese Cancer Association Presentation, Abstract #2125, Oct. 1, 2002, English translation of document cited in IDS.*
Hausmann, R., et al., Int. J. Legal Med., 112: 227-232, 1999.*
Sixty-first Annual Meeting of the Japanese Cancer Association, Oct. 1-3, 2002, Tokyo, Japanese Journal of Cancer Research, vol. 93, Supplement (Aug. 20, 2002).
Hollinger et al., Proc. Natl. Acad. Sci. USA, vol. 90, pp. 6444-6448, Jul. 1993.
Negri et al., "In Vitro and in vivo stability and anti-tumor efficacy of an anti-EGFR/anti-CD3 F(ab')2 bispecific monoclonal antibody," British Journal of Cancer, vol. 72, pp. 928-933 (1995).
Zhu et al., "High Level Secretion of a Humanized Bispecific Diabody from *Escherichia coli*," Biotechnology, vol. 14., pp. 192-196 (Feb. 1996).
Adair et al., "Humanization of the murine anti-human CD3 monoclonal antibody OKT3," Hum. Antibod. Hybridomas, vol. 5, Nos. 1 and 2, pp. 41-47 (1994).
Ferrini et al., "Targeting of T Lymphocytes Against EGF-Receptor+ Tumor Cells by Bispecific Monoclonal Antibodies: Requirement of CD3 Molecule Cross-Linking for T-Cell Activation," Int. J. Cancer, vol. 55, pp. 931-937 (1993).
M. R. Shalaby et al., "Development of Humanized Bispecific Antibodies Reactive with Cytotoxic Lymphocytes and Tumor Cells Overexpressing the HER2 Protooncogene," J. Exp. Med., vol. 175, pp. 217-225 (Jan. 1992).
Carter et al., "Humanization of anti-p185$^{HER2}$ antibody for human cancer therapy," Immunology, Proc. Natl. Acad. Sci. USA, vol. 89, pp. 4285-4289 (May 1992).
Zhu et al., "Remodeling domain interfaces to enchance heterodimer formation," Protein Science, vol. 6, pp. 781-788 (1997).
Abstracting Journal for 75th Annual Congress of The Japanese Biochemical Society, vol. 74, No. 8, Aug. 25, 2002.

* cited by examiner

Primary Examiner—Alana M. Harris
Assistant Examiner—Anne L Holleran
(74) Attorney, Agent, or Firm—Birch, Stewart, Kolasch & Birch, LLP

(57) ABSTRACT

The purpose of the present invention is to provide a diabody-type bispecific antibody, which is characterized by having low immunogenicity and high infiltrating activity into tumor tissues, and by being easily mass-produced at a low cost with use of microorganisms, and by being easily altered in function by means of genetic engineering. The diabody-type bispecific antibody shows a more remarkable effect than the conventional diabody-type bispecific antibodies and chemically synthesized bispecific antibodies even in a very low concentration and in the absence of the super antigen. The present invention is related to a diabody-type bispecific antibody, having a first specificity to a human epidermal growth factor (EGF) receptor and a second specificity to a surface antigen expressed by a cell having phagocytosis or cytotoxic activity, a single-chain polypeptide constituting the antibody or each region contained therein, a nucleic acid encoding the polypeptide, a replicable cloning vector or expression vector comprising the nucleic acid, a host cell transformed with the vector, and a pharmaceutical preparation comprising thereof.

9 Claims, 28 Drawing Sheets

FIG. 1

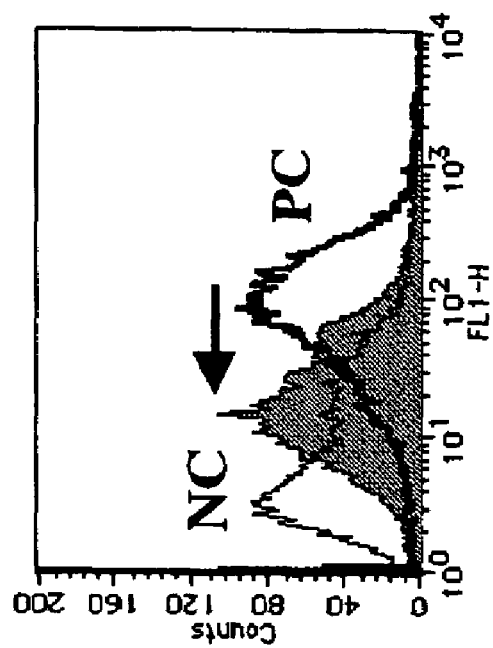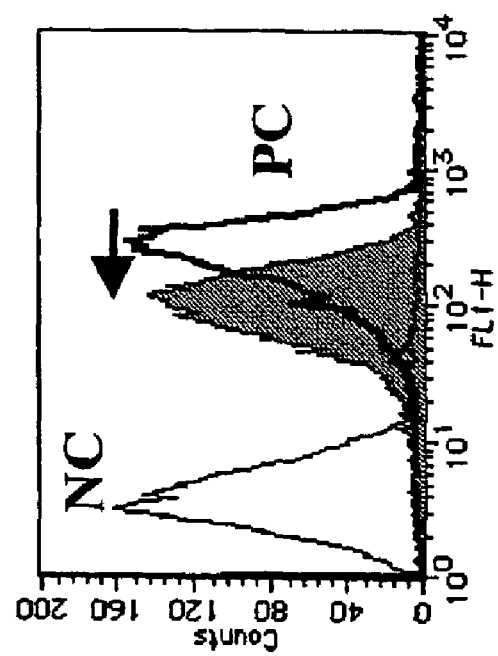
FIG. 6

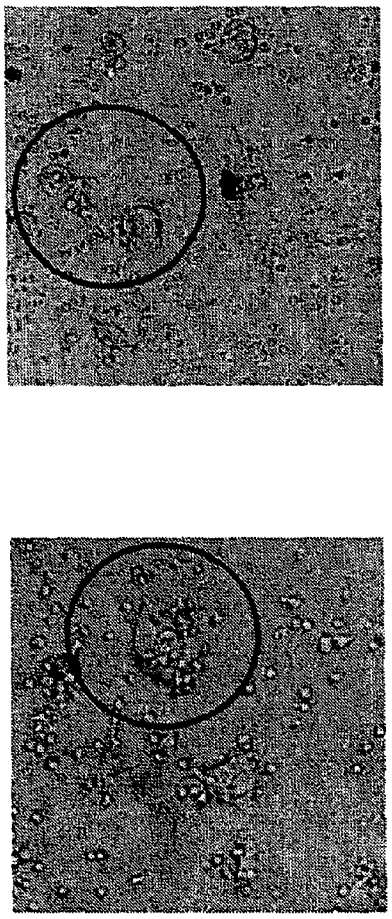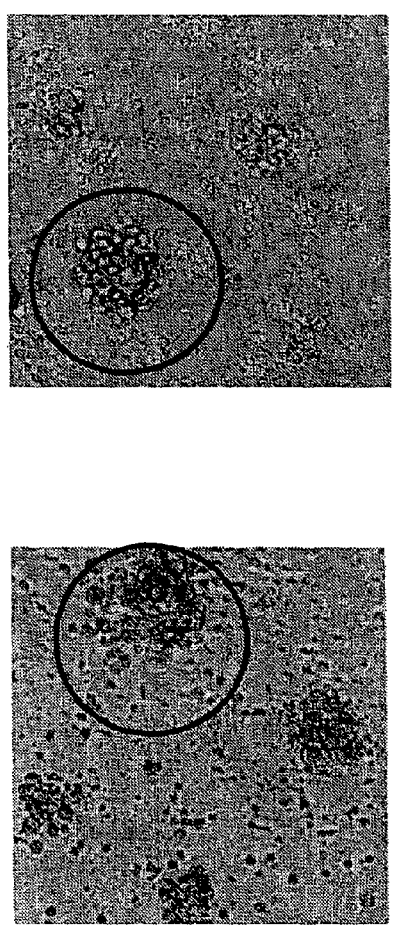
FIG. 9

VH

```
        10         20         30         40         50         60
CAGGTCCAACTGGTGCAGAGCGGCGGCGTGGCGTGCGTTGTGCAGCGGGCCGGGCCAGCCTGCGCCTG
 Q  V  Q  L  V  Q  S  G  G  G  V  V  Q  P  G  R  S  L  R  L
        70         80         90        100        110        120
TCTTGCAAAGCGAGCGGCTATACCTTTACGCGCTATACCATGCATTGGGTGCGCCAGGCG
 S  C  K  A  S  G  Y  T  F  T  R  Y  T  M  H  W  V  R  Q  A
       130        140        150        160 CDR2 170        180
CCGGGCAAAGGTCTCGAATGGATTGGCTATATTAACCCGTCTCGCGGCTATACCAACTAT
 P  G  K  G  L  E  W  I  G  Y  I  N  P  S  R  G  Y  T  N  Y
       190        200        210        220        230        240
AATCAGAAAGTGAAAGATCGTTTTACCATTAGCCGCGATAACTCTAAAAACACCGCGTTT
 N  Q  K  V  K  D  R  F  T  I  S  R  D  N  S  K  N  T  A  F
       250        260        270        280 CDR3 290        300
CTGCAGATGGATAGCCTGCGCCCGGAAGATACCGGCGTGTATTTTTGCGCGCGTTACTAT
 L  Q  M  D  S  L  R  P  E  D  T  G  V  Y  F  C  A  R  Y  Y
       310        320        330        340        350
GATGACCATTATAGCCTTGATTATTGGGGCCAGGGCACCCCGGTGACCGTTAGCTCG
 D  D  H  Y  S  L  D  Y  W  G  Q  G  T  P  V  T  V  S  S
```

VL

```
        10         20         30         40         50         60
GATATCCAGATGACCCAGAGCCCGAGCCTCTGAGCGCGTCTGTGGGCGATCGCGTGACC
 D  I  Q  M  T  Q  S  P  S  S  L  S  A  S  V  G  D  R  V  T
        70    CDR1 80         90        100        110        120
ATTACGTGCAGCGCGTCTAGCTCTGTGAGCTATATGAACTGGTACCAGCAAAACCCAGGC
 I  T  C  S  A  S  S  S  V  S  Y  M  N  W  Y  Q  Q  T  P  G
       130        140        150    CDR2 160        170        180
AAAGCGCCCAAAACGCTGGATTATGATACCAGCAAACTGGCGAGCGGCGTGCCGAGCCGC
 K  A  P  K  R  W  I  Y  D  T  S  K  L  A  S  G  V  P  S  R
       190        200        210        220        230        240
TTTAGCGGCTCTGGTAGCGGCACCGATTACTTTACCATTAGCTCTCTGCAGCCGGAA
 F  S  G  S  G  S  G  T  D  Y  F  T  I  S  S  L  Q  P  E
       250        260    CDR3 270        280        290        300
GATATTGCGACCTATTACTGCCAGCAATGGAGCTCTAACCCGTTTACCTTTGGCCAGGGT
 D  I  A  T  Y  Y  C  Q  Q  W  S  S  N  P  F  T  F  G  Q  G
       310        320
ACCAAACTGCAGATTACCCGCGCG
 T  K  L  Q  I  T  R  A
```

```
         10         20         30         40         50         60
CAGGTGCAACTGGTTCAGAGAGTCAGGGGCGCCGAAGTGAAAAAGCCCGGGGCGTCGGTTAAAGTG
 Q  V  Q  L  V  Q  S  G  A  E  V  K  K  P  G  A  S  V  K  V
         70         80         90        100 CDR1 110        120
AGCTGCAAAGCCTCAGGCTATACCTTCACCAGCTACTGGATGCAT TGGGTCGCCCAGGCC
 S  C  K  A  S  G  Y  T  F  T  S  Y  W  M  H  W  V  R  Q  A
        130        140        150        160        170 CDR2 180
CCGGGTCAGGGCCTGGAATGGATGGGTAAC ATTTATCCGGGTAGTGGGCACCAACTAT
 P  G  Q  G  L  E  W  M  G  N  I  Y  P  G  S  G  G  T  N  Y
        190        200        210        220        230        240
GCGGAAAAATTTAAGAAC CGCGTGACCATGACCCGGGATACCAGCATTTCGACGGCCTAT
 A  E  K  F  K  N  R  V  T  M  T  R  D  T  S  I  S  T  A  Y
        250        260        270        280        290 CDR3 300
ATGGAACTGAGCCGCCTGCGCAGCGATGACACCGCCGTGTATTACTGC GCGCGCAGTCG
 M  E  L  S  R  L  R  S  D  D  T  A  V  Y  Y  C  A  R  S  G
        310        320        330        340        350
GGTCCGTATTTTTTCGATTAC TGGGGCCAGGGTACGCTGGTTACCGTGAGCTCG
 G  P  Y  F  F  D  Y  W  G  Q  G  T  L  V  T  V  S  S
```

VL

```
         10         20         30         40         50         60
GATATTGTGATGACCCAGAGACCGTCTGAGCCTGCCGCGTGACCCCAGGCGTGAACCGGCGTCG
 D  I  V  M  T  Q  S  P  L  S  L  P  V  T  P  G  E  P  A  S
         70 CDR1 80         90        100        110        120
ATTAGCTGC CGCAGCTCGCAGAACATCGTGCATAATAACGGCATTACCTATCTGGAA TGG
 I  S  C  R  S  S  Q  N  I  V  H  N  N  G  I  T  Y  L  E  W
        130        140        150        160        170 CDR2 180
TATCTGCAGAAACCCGGCCAAAGCCCGCAGCTGCTTATTTAT AAGGTGAGCGATCGCTTT
 Y  L  Q  K  P  G  Q  S  P  Q  L  L  I  Y  K  V  S  D  R  F
        190        200        210        220        230        240
AGC GGCGTGCCGGATCGCTTTTCGGGCAGCGGTAGTGGCACCGATTTTACGCTGAAAATT
 S  G  V  P  D  R  F  S  G  S  G  S  G  T  D  F  T  L  K  I
        250        260        270        280        290 CDR3 300
AGCCGCGTGGAAGCGGAGGATGTTGGCGTGTATTACTGC TTCAGGGCAGCCATATCCCG
 S  R  V  E  A  E  D  V  G  V  Y  Y  C  F  Q  G  S  H  I  P
        310        320        330        340
CCAACC TTCGGCCAAGGCACCAAAGTGGAAATTAAACGCGCG
 P  T  F  G  Q  G  T  K  V  E  I  K  R  A
```

FIG. 22

```
             FR1                              CDR1    FR2                   CDR2
5H           QVQLQQSGSEMARPGASVKLPCKASGDTFT    SYWMH   WVKQRHGHGPEWIG        NIYPGSGGTNYAEKFKN
h5H          QVQLVQSGAEVKKPGASVKVSCKASGYTFT    SYWMH   WVRQAPGQGLEWMG        NIYPGSGGTNYAEKFKN
h5H-m01      ------------------------------    -----   -------------I-       -----------------
h5H-m02      ------------------------------    -----   -------------I-       -----------------
h5H-m03      ------------------------------    -----   -------------I-       -----------------
h5H-m04      ---------------------D--------    -----   -------------I-       -----------------
h5H-m05      ------------------------------    -----   -------------I-       -----------------
h5H-m06      ------------------------------    -----   -------------I-       -----------------
h5H-m07      ------------------------------    -----   -------------I-       -----------------
h5H-m08      ------------------------------    -----   -------------I-       -----------------
h5H-m09      ------------------------------    -----   -------------I-       -----------------
h5H-m10      ------------------------------    -----   -------------I-       -----------------

FR3                              CDR3         FR4
5H           KVTLTVDRSSRTVYMHLSRLTSEDSAVYYCTR   SGGPYFFDY   WGQGTTLTVSS
h5H          RVTMTRDTSISTAYMELSRLRSDDTAVYYCAR   SGGPYFFDY   WGQGTLVTVSS
h5H-m01      --------------------------------   ---T-----   -----------
h5H-m02      K----V--------------------------   ---------   -----------
h5H-m03      K----V--------------------------   ---T-----   -----------
h5H-m04      K----V--------------------------   ---------   -----------
h5H-m05      K----V--------------------------   ---T-----   -----------
h5H-m06      K----V--------------------------   ---------   -----------
h5H-m07      K--L-V-R------------------------   ---T-----   -----------
h5H-m08      K--L-V-R------------------------   ---------   -----------
h5H-m09      K--L-V-R------------------------   ---T-----   -----------
h5

DIABODY-TYPE BISPECIFIC ANTIBODY

This nonprovisional application claims priority under 35 U.S.C. § 119(a) on Patent Application No(s). 2003-038643 filed in JAPAN on Feb. 17, 2003, which is(are) herein incorporated by reference.

FIELD OF THE INVENTION

The present invention is related to a novel diabody type bispecific antibody, which may be used in a cancer-specific immunotherapy, a single-chain polypeptide constituting the antibody or each region contained therein, a nucleic acid encoding the polypeptide, a method for the production of the antibody, use of them as a pharmaceutical preparation, etc.

BACKGROUND OF THE INVENTION

Surgical resection, chemotherapy, radiotherapy and immunotherapy have been mainly used alone or together as a treating method of cancer (malignant tumor). Although the immunotherapy is still in a developmental stage, it has a lot of potentialities and is therefore expected to make further progress in the near future.

The immunotherapy specific to the cancer means a treating method in which a cytotoxic activity is affected only upon cancer cells. As a drug showing the cytotoxic activity is combined with an antibody to have directivity in this therapy, it is now called a "missile therapy." Studies have now been carried out to find an antigen that will be effectively used for the preparation of the antibody with a minimum of side effects by targeting as the antigen a substance that is abnormally expressed in the cancer cells or that will change according to malignant alternation or canceration of cells. Such antigen is called a cancer-associated antigen.

Among antibodies with multiple specificity, an antibody with bispecificity (Bispecific Antibody: BsAb) is now studied intensively. The bispecific antibody can bind specifically to two different kinds of antigens so that it will be utilized as a therapeutic agent having a specific anti-cancer effect. A diabody is a minimum unit of the above bispecific antibody. It was developed by utilizing the property that the variable region in the heavy chain (VH) and the variable region in the light chain (VL) derived from the same parent antibody will form a hetero-dimer through non-covalent bond (Hollinger, et al., Proc. Natl. Acad. Sci. USA 90, 6444-6448, 1993).

A diabody-type bispecific antibody is characterized by having low immunogenicity and high infiltrating activity into tumor tissues due to its low molecular weight (ca. 60,000), and by being easily mass-produced at a low cost with use of microorganisms such as *E. coli*, and by being easily altered in function by means of genetic engineering.

It is therefore strongly desired to develop the diabody-type bispecific antibody that may resolve problems encountered in the conventional cancer therapies, especially the problems that it is impossible to completely remove cancer cells located at a site where the structure of tissues is complicated and that there is no way to remove the remaining cancer cells after a surgical operation.

Up to now, as an example of the diabody-type bispecific antibody, a fused protein has been developed. It has bispecificity derived from an antibody against a glycoprotein MUC1 often observed on adenocytes and an anti-CD3 antibody, and further contains a super antigen such as cellular enterotoxin in the same polypeptide as the variable region of the antibody (PCT Publication No. WO02/06486).

However, since the conventional diabody-type bispecific antibodies are a recombinant protein produced with use of microorganism, they tend to be inferior in effectiveness and stability after administration to the bispecific antibodies chemically synthesized. The conventional diabody-type bispecific antibodies also have some problems or disadvantages such as that they have to be produced in a high concentration in order to obtain the same effects as those by the bispecific antibodies chemically synthesized.

On the other hand, it was already reported that an antibody specific to HER-2/neu(c-erb-2), one of epidermal growth factor receptors (EGFR) that are a cell membrane-bound glycoprotein, could reduce the tumor by about 20% in breast cancer patients.

The present inventors have studied to resolve the above problems so as to develop a novel diabody-type bispecific antibody that shows an excellent effect, and finally succeeded in preparing a diabody-type bispecific antibody showing a more remarkable effect than the conventional diabody-type bispecific antibodies and chemically synthesized bispecific antibodies even in a very low concentration and in the absence of the super antigen.

SUMMARY OF THE INVENTION

A first aspect of the present invention relates to a diabody-type bispecific antibody, having a first specificity to a human epidermal growth factor (EGF) receptor and a second specificity to a surface antigen expressed by a cell having phagocytosis or cytotoxic activity.

A second aspect of the present invention relates to either of the two kinds of a single-chain polypeptide constituting the above diabody-type bispecific antibody, or a polypeptide constituting each region contained in the single-chain polypeptide.

A third aspect of the present invention relates to a nucleic acid encoding the above single-chain polypeptide or each region contained therein.

A fourth aspect of the present invention relates to a replicable cloning vector or expression vector comprising the above nucleic acid.

A fifth aspect of the present invention relates to a host cell transformed with the above vector.

A sixth aspect of the present invention relates to a method for the production of the above single-chain polypeptide, comprising culturing the above host cell to express the nucleic acid in it, collecting and purifying the above single-chain polypeptide.

A seventh aspect of the present invention relates to a method for the production of the above diabody-type bispecific antibody, comprising assembling the single-chain polypeptides to form the above diabody-type bispecific antibody, and separating and collecting the diabody-type antibody.

A eighth aspect of the present invention relates to a pharmaceutical preparation comprising an active ingredient selected from the group consisting of the above diabody-type bispecific antibody, the above single-chain polypeptide, the above nucleic acid, the above vector and the above host cell.

A ninth aspect of the present invention relates to a method for increasing the production of cytokines by the cells having phagocytosis or cytotoxic activity, comprising adding the above diabody-type bispecific antibody to a culture system containing the cells having phagocytosis or cytotoxic activity and tumor cells expressing the human EGF receptors.

BRIEF DESCRIPTION OF THE DRAWINGS

FIG. 1 shows amino acid sequences of the variable regions of anti-EGFR antibody 528 (SEQ ID NOS: 25 and 26).

FIG. 6 shows the results of inhibition test of Ex3 by Flow Cytometry.

FIG. 9 are microscopic photos showing inhibition of the accumulation by the addition of IgG.

FIG. 21 shows amino acid sequences of the variable regions of a humanized antibody OKT3 (SEQ ID NOS: 27 and 28).

FIG. 22 shows amino acid sequences of the variable regions of a humanized antibody 528 (SEQ ID NOS: 29 and 30).

FIG. 26 shows introduction of a site-specific mutation into h5H (SEQ ID NOS: 25, 29 and 31-40).

BEST MODE FOR CARRYING OUT THE INVENTION

The diabody-type bispecific antibody in the present specification means a small fragment of an antibody having two antigen-binding sites. The fragment contains the variable region of the heavy chain (VH) and the variable region of the light chain (VL) in the same polypeptide chain. In a typical diabody, these two regions (domains) in the same chain are linked together via a linker that is too short to pair the above two domains, so that each domain will be paired with its complementary domain of the other chain to form the two antigen-binding sites together, respectively. With respect to the diabody and techniques for its production, one may refer to U.S. Pat. No. 4,704,692, U.S. Pat. No. 4,946,778, U.S. Pat. No. 5,990,275, U.S. Pat. No. 5,994,511, U.S. Pat. No. 6,027,725, EP No. 404,097, WO93/11161, and Hollinger, et al., Proc. Natl. Acad. Sci., USA 90: 6444-6448 (1993), the disclosures of which are incorporated herein by reference, in their entirety to the same content as if each individual patent and document were specifically and individually incorporated by reference.

Figure 2:
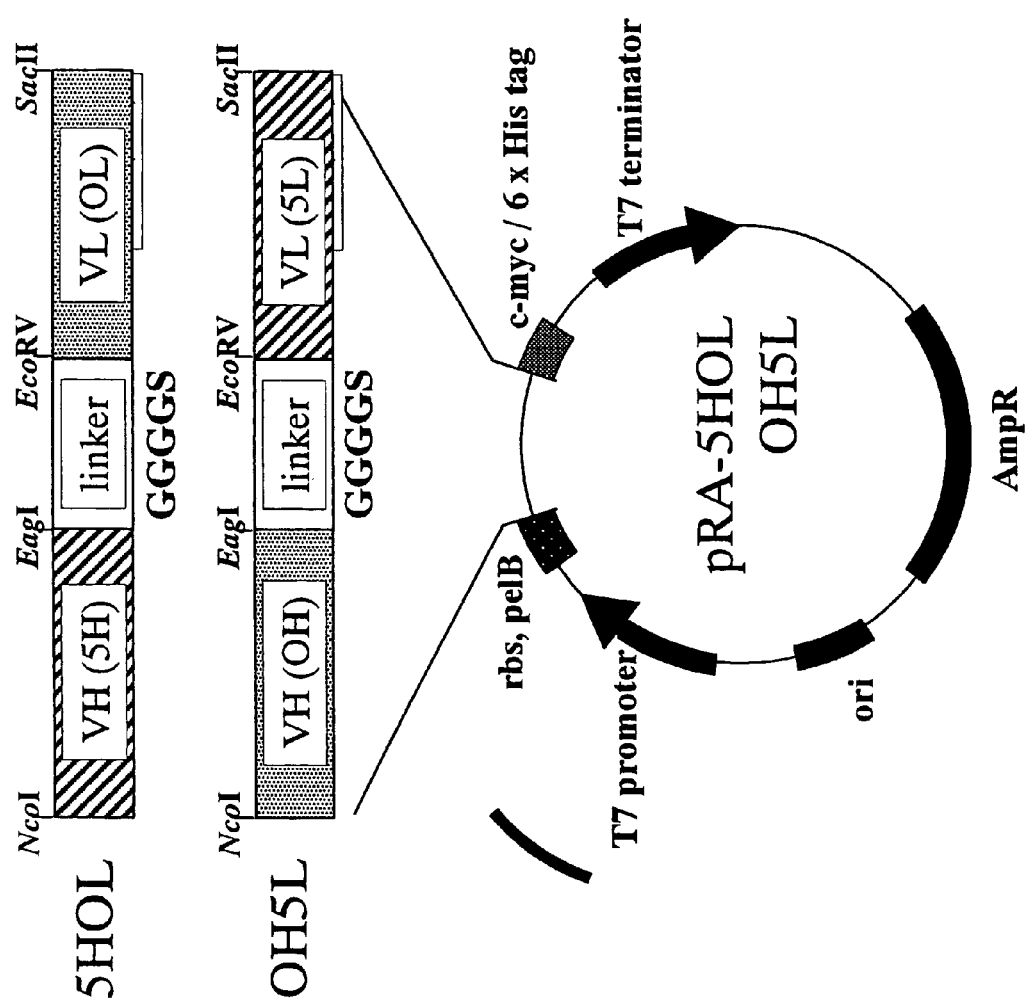
FIG. 2 is a schematic chart showing the structure of Ex3 expression vectors of pRA-5HOL and pRA-OH5L.

More specifically, the term "diabody-type bispecific antibody" refers to a fused protein having two different antigen-recognizing functions, consisting of a first polypeptide (i) having in the same peptide chain an antigen-binding site (a) of the variable region of the heavy chain derived from a first antibody and an antigen-binding site (b) of the variable region of the light chain derived from a second antibody, and a second polypeptide (ii) having in the same peptide chain an antigen-binding site (c) of the variable region of the light chain derived from the first antibody and an antigen-binding site (d) of the variable region of the heavy chain derived from the second antibody, as described in FIG. 2 of PCT Publication No. WO02/06486.

According to the present invention, the first antibody has the specificity to a human epidermal growth factor (EGF) receptor, and the second antibody has the specificity to the surface antigen expressed by a cell having phagocytosis or cytotoxic activity. As demonstrated by the examples in the present specification, the diabody-type bispecific antibody according to the present invention shows an excellent cytotoxic activity both in vitro and in vivo.

Although there is no limitation with respect to sources or kinds of the antibodies used in the above diabody-type bispecific antibody, they are usually derived from mammalians such as human, mouse and rat. Monoclonal antibodies produced by hybridomas are also preferred since they recognize a single antigenic site with a high specificity to it.

Human epidermal growth factor receptor (hEGFR) is a membrane-bound glycoprotein with a molecular weight of about 170 kDa and belongs to EGF family. Four kinds of the hEGFR, i.e., HER-1/Erb1, HER-2/Erb2, HER-3/Erb3 and HER-4/Erb4, have been identified until now. HER-2/Erb2 is expressed in 30-40% of the adenocarcinoma such as pulmonary carcinoma, gastric carcinoma, colon and rectum carcinomas, breast carcinoma, and ovarian carcinoma. HER-1/Erb1 is expressed in more than 80% of neck cancer, in 14-91% of breast cancer, in 40-80% of non-small cell lung cancer, in 25-77% of colon and rectum carcinomas, in 30-50% of pancreatic cancer, in 40-80% of prostatic cancer, in 35-70% of ovarian cancer, and in 33-74% of gastric carcinoma. EGF receptors are a surface antigen of human cancers or cancer-associated antigen.

The term "human epidermal growth factor receptor" as used herein refers to at least the above four kinds of EGF receptors identified up to now. The antibodies against the human EGFR are already known to those skilled in the art. One of the preferred diabody-type bispecific antibodies according to the present invention has the first specificity to the human EGF receptor 1 (Her1). As one of the antibodies that can provide such specificity, there may be mentioned an anti-human EGF receptor antibody 528 that is produced by mouse B cell hybridoma 528. Accordingly, the first specificity of the diabody-type bispecific antibody according to the present invention is derived from the variable regions in the heavy and light chains of the anti-human EGF receptor antibody 528 (FIG. 1).

The term "a cell having phagocytosis or cytotoxic activity" as used herein includes T cells such as NK cell, macrophage, and T-LAK cell, preferably T-LAK cell that is also known as a cytotoxic T cell. The surface antigen expressed by these cells includes CD2, CD3, CD4, CD5, CD6, CD8, CD16, CD28, and CD44, preferably CD3 expressed by the cytotoxic T cell.

The monoclonal antibodies against these surface antigens include those known in the art such as OKT3, T3, Leu4, T11, OKT11, Leu5b, NU-T1, OKT4, Leu3a, NU-TH/I, T8, OKT8, Leu2a and NU-Ts/c, preferably OKT3, T3 and Leu4. Accordingly, the second specificity of the diabody-type bispecific antibody according to the present invention is derived from the variable regions in the heavy chain and the light chain of anti-CD3 antibody OKT3.

In addition to the above commercially available antibodies, the antibodies that will provide the variable regions of the diabody-type bispecific antibody according to the present invention can be prepared by various methods well known in the art with use of the human EGFRs or the cells having phagocytosis or cytotoxic activity as an immunogen.

For example, polyclonal antibodies may be produced in the body of animals such as mouse by subcutaneously or intraperitoneally injecting the immunogen in the animals several times optionally in combination with an adjuvant.

On the other hand, monoclonal antibodies may be obtained from a substantially homogeneous population in accordance with a method first described in Kohler & Milstein, Nature 256: 495 (1975), or alternatively by means of a recombinant DNA technique (U.S. Pat. No. 4,816,567).

Furthermore, human antibodies may be prepared in the body of a transgenic animal (e.g., mouse). Please refer to, for example, Duchosal et al., Nature 355:258 (1993); Jakobovits et al., Proc. Natl. Acad. Sci. USA 90:2551 (1993); Jakobovits et al., Nature 362:255-258 (1992); Bruggermann et al., Year in Immunol. 7:33 (1993). Human antibodies may be also derived from phage display libraries (Marks et al., J. Mol. Biol. 222:581-597 (1991); Hoogenboom et al., J. Mol. Biol. 227:381 (1991); Hoogenboom et al., Immunol. Rev. 130:41-68 (1992); Vaughan et al., Nature Biotech. 14:309 (1996)).

The above antibodies and the fragment thereof may be further isolated from antibody phage library in accordance with the technique described in Cafferty et al., Nature, 348: 552-554 (1990). Clackson et al., Nature, 352:624-628 (1991) and Mark et al., J. Mol. Biol. 222:581-597 (1991) disclose the isolation of mouse and human antibody from the phage library, respectively. The above antigens may be used to select an appropriate antibody or fragment thereof. Other techniques known to those skilled in the art may be optionally used in the present invention, which include chain shuffling method to produce a human antibody with a high affinity (the order of nM) (Mark et al., Bio/Technol. 10: 779-783 (1992), combinatorial infection and in vivo recombination method to construct a very large phage library (Waterhouse et al., Nuc. Acids Res., 21:2265-2266 (1993).

The diabody-type bispecific antibody according to the present invention may comprise a linker that links the variable region of the heavy chain (VH) and the variable region of the light chain (VL) with each other. The term "linker" as used herein refers to an oligopeptide or polypeptide that combines VH and VL together to give a single-chain polypeptide. The linker is preferably a peptide linker. Any linker known in the art or modified therefrom may be optionally selected and used in the present invention as long as it can operably combine the two polypeptides together to give the single-chain polypeptide. The peptide linker according to the present invention may have about 1-50 amino acids, preferably about 2-30 amino acids, more preferably about 2-20 amino acids. The term "operably combine" as used herein refers to an appropriate folding of the polypeptide to give a fused protein having such a three-dimensional structure as to mimic the function of the original protein (the function derived from the original polypeptide or protein) such as all or part of its biological activity.

The length of the linker is selected so as to give a desired activity to the single-chain polypeptide or fused protein while depending on their properties. The linker, however, should be long enough to fold the resulting single-chain polypeptide so as to give the desired biological activities. The length of the linker may be experimentally determined by testing a series of single-chain polypeptides prepared by using linkers with different lengths. The documents listed above with respect to the diabody and techniques for its production may be referred to for the linker as well.

The VH region and VL region may be arbitrarily allocated in the single-chain polypeptide, including VL(N-end)-Linker-VH(C-end) construct and VH (N-end)-Linker-VL (C-end) construct.

The diabody-type bispecific antibody according to the present may be humanized. The humanized antibody is clinically very advantageous since its potentiality of acting as immunogenicity upon administration into human body has been lowered by using the regions with specific reactivity that is derived from mouse antibodies and the like, and the other regions that are derived from human antibodies.

The term "humanized antibody" as used herein means a human immunoglobulin (a recipient antibody) in which at least part of the residues of complementary-determining region (CDR) is replaced with residues derived from the CDR of a non-human animal antibody (a donor antibody) that has a desired specificity, affinity and capability, such as those of mouse, rat, and rabbit. In some cases, the residue(s) of a Fv framework (FR) in the human immunoglobulin is replaced with residue(s) of the corresponding non-human antibody. The humanized antibody may further comprise a residue that is not found in the recipient antibody or the introduced CDR or framework. These changes are made in order to optimize or improve the properties of the resulting antibody. More detailed information on these changes are referred to Jones et al., Nature 321, 522-525 (1986); Reichmann et al., Nature 332, 323-329 (1988); EP-B-239400; Presta, Curr. Op. Struct. Biol 2, 593-596 (1992); and EP-B-451216.

The humanized antibody may be prepared in accordance with any methods known to those skilled in the art, for example, by analyzing various conceptual humanized preparations based on three-dimensional immunoglobulin models of the recipient antibody and donor antibody, and analyzing them. The three-dimensional immunoglobulin models are well known in the art, being referred to, for example, WO92/22653.

Thus, one example of the humanized diabody-type bispecific antibody according to the present invention is that wherein the complementary determining region (CDR) in the variable regions are derived from a mouse antibody, and the other parts are derived from a human antibody. One preferable example is therefore a diabody-type bispecific antibody having at least one CDR selected from the amino acid sequences of CDR1, CDR2 and CDR3 in the variable regions derived from a humanized anti-CD3 antibody OKT3 represented in FIG. 21 and having at least one CDR selected from the amino acid sequences of CDR1, CDR2 and CDR3 in the variable regions derived from a humanized anti-human EGF receptor antibody 528 represented in FIG. 22.

More preferable example is a diabody-type bispecific antibody, wherein the variable regions in the heavy chain and light chain derived from the humanized anti-CD3 antibody OKT3 have an amino acid sequence represented in FIG. 21 (SEQ ID No. 27 and 28) and, the variable regions in the heavy chain and light chain derived from the humanized anti-human EGF receptor antibody 528 have an amino acid sequence represented in FIG. 22 (SEQ ID No. 29 and 30).

The activity or function of the resulting antibody may be deteriorated due to the humanization. The activity or function of the diabody-type bispecific antibody according to the present invention may be therefore improved by being provided with a site-specific mutation at an appropriate position in the single-chain polypeptide, for example, at a position in the framework which can affect the CDR structure, such as in canonical sequence or vernier sequence. The antibody obtained by such site-specific mutation is included in the diabody-type bispecific antibody according to the present invention.

As described above, the diabody-type bispecific antibody according to the present invention consists of two kinds of the single-chain polypeptides. The present invention relates therefore also to each single-chain polypeptide and to a polypeptide constituting each region (for example, the variable region derived from each antibody) contained in the single-chain polypeptide. The single-chain polypeptide has the variable region in the heavy chain derived from a first (or second) antibody, the variable region in the light chain derived from a second (or first) antibody and the linker binding them to each other. It may further optionally contain bacterial enterotoxin such as *staphylococcus* enterotoxin, *E. coli* enterotoxin, cholera enterotoxin, and their derivatives. Various peptide tags (c-myc and His-tag, for example) known in the art may be contained at its end, etc.

However, it is well known that these super antigens may possibly cause cytokine-depending toxin shock syndromes due to their strong affinity towards MHC class II. On the contrary, the diabody-type bispecific antibody according to the present invention shows remarkably high cytotoxic activity even without such super antigen, and advantageously avoids the above potential risk due to the super antigen.

In accordance with a method known to those skilled in the art, a nucleic acid encoding the single-chain polypeptide or each region contained therein may be obtained, and its base sequence may be determined, by using, for example, an oligonucleotide probe specifically binding to a gene encoding the heavy and light chains of the mouse antibody (R. Orlandi et al., Proc. Natl. Acad. Sci., USA 86: 3833-3837 (1993)). The hybridomas producing the above monoclonal antibodies may be used as DNA source in these methods.

More specifically, the nucleic acid encoding the single-chain polypeptide may be prepared by replacing VH or VL in a single-chain Fv (or "scFv") already constructed and known in the art or in a known diabody-type bispecific antibody with another VH or VL derived from an antibody having different specificity. The term "scFv" as used herein means a single-chain polypeptide having VH domain and VL domain of an antibody within a single-chain polypeptide. Usually the scFv polypeptide has a linker between the two domains in order to give a structure necessary for showing antigen-binding activity. Rosenburg and Moore (Ed.), "The Pharmacology of Monoclonal Antibodies," Vol. 113, Springer-Verlag, New York pp. 269-315 (1994) may be referred to with respect to scFv.

Furthermore, the nucleic acid encoding the variable regions in the single-chain polypeptide of the diabody-type bispecific antibody may be synthesized by means of an overlapping PCR method based on a pre-determined amino acid sequence. The nucleic acid used herein has no limitation in its chemical structure or preparation route, as long as it is a molecule encoding the single-chain polypeptide, including gDNA, cDNA chemically-synthesized DNA and mRNA.

Specifically, the nucleic acid according to the present invention may be isolated from cDNA library by means of hybridization or PCR based on the sequences disclosed in literatures. The thus isolated DNA may be inserted in an expression vector, with which a host cell such *E. coli*, COS cell, CHO cell or myeloma not expressing immunoglobulin are transfected to synthesize a monoclonal antibody in the thus transformed host cells.

PCR may be carried out in accordance with a method known in the art, or substantially the same or altered methods. The methods disclosed in, for example, R. Saiki, et al., Science, 230:1350, 1985; R. Saiki, et al., Science, 239:487, 1988; H. A. Erlich ed., PCR Technology, Stockton Press, 1989; D. M. Glover et al., ed., "DNA Cloning," $2^{nd}$. ed., Vol. 1, (The Practical Approach Series), IRL Press, Oxford University Press (1995); M. A. Innis et al., ed., "PCR Protocols: a guide to methods and applications," Academic Press, New York (1990); M. J. McPherson, P. Quirke and G. R. Taylor (Ed.), PCR: a practical approach, IRL Press, Oxford (1991); M. A. Frohman e al., Proc. Natl. Acad. Sci. USA, 85, 8998-9002 (1988), and their modified and altered methods may be used in the present invention. PCR may be performed with use of a commercially available kit in accordance with manufacturer's protocols.

Hybridization may be referred to L. Grossman et al. (ed.), "Methods in Enzymology", Vol. 29 (Nucleic Acids and Protein Synthesis, Part E), Academic Press, New York (1974). The sequencing method of nucleic acids such as DNA may be referred to Sanger et al., Proc. Natl. Acad. Sci. USA 74:5463-5467 (1977). A general method for recombinant DNA techniques may be referred to J. Sambrook, E. F. Fritsch & T. Maniatis (ed.), "Molecular Cloning: A Laboratory Manual ($2^{nd}$ edition)", Cold Spring Harbor Laboratory Press, Cold Spring Harbor, N.Y. (1989) and D. M. Glover et al. (ed.), $2^{nd}$ ed., Vol. 1 to 4 (The Practical Approach Series), IRL Press, Oxford University Press (1995).

The nucleic acid encoding the single-chain polypeptide or each region contained therein may be modified or altered so that it will optionally encode a desired peptide or amino acid depending on the purpose. The techniques for such modification or alternation are disclosed in Mutagenesis: a Practical Approach, M. J. McPherson (ed.), IRL Press, Oxford, UK (1991), including a site-specific mutagenesis introduction method, cassette mutagenesis induction method and PCR mutagenesis method.

The term "modification (or alternation)" as used herein refers to insertion, deletion or substitution of base(s) in at least one codon encoding an amino acid residue in the originally obtained nucleic acid. It includes alternation of the amino acid sequence per se of the single-chain polypeptide by replacing a codon encoding the original amino acid with a codon encoding another amino acid. The single-chain polypeptide constituting the humanized diabody-type bispecific antibody may be obtained in this way.

Alternatively, the nucleic acid encoding the single-chain polypeptide may be altered without changing the amino acid per se, by using a codon suitable for a host cell (an optimum codon). With the use of the optimum codon, expression efficiency of the single-chain polypeptide in the host cell will be improved.

The linker and super antigen may be optionally introduced into the single-chain polypeptide constituting the diabody-type bispecific antibody according to the present invention by means of any techniques well known in the art such as genetic engineering technique including recombinant technology and chemical synthesis of peptides.

The single-chain polypeptide may be produced by various methods well known in the art such as genetic engineering technique and chemical synthesis. The genetic engineering technique includes constructing a replicable cloning vector or expression vector, transforming the host cell with the vector, culturing the transformed host cell to express the nucleic acid in it, collecting and purifying the single-chain polypeptide. The vector usually comprises the nucleic acid encoding one of the two single-chain polypeptides constituting the diabody-type bispecific antibody according to the present invention. In such case, the resulting two kinds of the vectors are preferably introduced into the same host cell. Alternatively, the two kinds of nucleic acid encoding the different single-chin polypeptide from each other may be comprised in the same vector.

The term "replicable expression vector" or "expression vector" as used herein refers to a piece of DNA (usually double-stranded) that may comprise a fragment of a foreign DNA fragment inserted therein. The foreign DNA is also defined as a "heterologous DNA", which can not be found naturally in a host cell in interest. The vector is used to carry or convey the foreign or heterologous DNA into an appropriate host cell. Once the vector is introduced into the host cell, it may be replicated independently from a chromosomal DNA of the host cell to produce copies of the vector and foreign DNA inserted therein. The vector also comprises elements essential for translating the foreign DNA into a polypeptide so that the polypeptide molecules encoded by the foreign DNA will be synthesized very quickly.

The above vector means a DNA construct comprising an appropriate control sequence and DNA sequence that are operably linked together (i.e., linked together so that the foreign DNA can be expressed). The control sequence includes a promoter for transcription, an optional operator sequence to regulate the transcription, a sequence encoding an appropriate mRNA ribosome-biding site, an enhancer, a polyadenylation sequence, and a sequence controlling the termination of transcription and translation. The vector may further comprise various sequences known in the art, such as a restriction enzyme cleaving site, a marker gene (selection gene) such as a drug-resistant gene, a signal sequence, and a leader sequence. These sequences and elements may be optionally selected by those skilled in the art depending on the kinds of the foreign DNA and host cell, and conditions of culture medium.

The vector may be in any form such as a plasmid, phage particle, or just simply genomic insert. Once the appropriate host cell is transformed with the vector, the vector will be replicated or function independently from the genome of the host cell, or the vector will alternatively be integrated into the genome of the cell.

Any cell known in the art may be used as the host cell, for example, there may be mentioned procaryotic cells such as including *E. coli*, eucaryotic cells such as mammalian cells such Chinese hamster ovary (CHO) cell and human cells, yeast, and insect cells.

Although the single-chain polypeptide obtained by the expression in the host cell is usually secreted and collected from the culture medium, it may be also collected from cell lysate when it is directly expressed without a secretion signal. In case the single-chain polypeptide has a membrane-binding property, it may be released from the membrane with an appropriate surfactant such as Triton-X100.

Purification of the polypeptide may be carried out by any method known to those skilled in the art such as centrifugation, hydroxyapatite chromatography, gel electrophoresis, dialysis, separation on ion-exchange chromatography, ethanol precipitation, reverse phase HPLC, silica chromatography, heparin-sepharose chromatography, anion- or cation-resin chromatography such as polyaspartic acid column, chromato-focusing, SDS-PAGE, precipitation with ammonium sulfate, and affinity chromatography. The affinity chromatography, which utilizes affinity with a peptide tag of the single-chain polypeptide, is one of the preferred purification techniques with a high efficiency.

Since the collected single-chain polypeptide may be often included in an insoluble fraction, the polypeptide is preferably purified after being solubilized and denatured. The solubilization treatment may be carried out with the use of any agent known in the art, including alcohol such ethanol, a dissolving agent such as guanidine hydrochloride and urea.

The diabody-type bispecific antibody according to the present invention is produced by assembling the single-chain polypeptides, and separating and collecting the thus formed diabody-type antibody.

Assembling treatment brings the single-chain polypeptide back in an appropriate spatial arrangement in which a desired biological activity is shown. Thus, since this treatment brings the polypeptides or domains back into an assembling state, it may be considered "re-assembling." It may be also called "re-constitution" or "refolding" in view of gaining the desired biological activity.

The assembling treatment may be carried out by any method known in the art preferably by gradually lowering the concentration of a denaturing agent such as guanidine hydrochloride in a solution comprising the single-chain polypeptide by means of dialysis. During these processes, an anti-coagulant or oxidizing agent may be optionally added in a reaction system in order to promote the oxidation. The separation and collection of the formed diabody-type bispecific antibody may be done by any method known in the art as well.

A pharmaceutical preparation according to the present invention comprises an active ingredient selected from the group consisting of the diabody-type bispecific antibody, especially the humanized one, the single-chain polypeptide, the nucleic acid, the vector, and the host cell described in the above. As shown by the examples in the present specification, since the active ingredient has an activity of eliminating, hurting, damaging and/or reducing tumor cells expressing EGFR in vitro and in vivo, the present pharmaceutical preparation is used as an anti-tumor agent.

Furthermore, it is demonstrated by the examples in the present specification that co-existence of the diabody-type bispecific antibody with the tumor cells expressing human EGFR and the cells having phagocytosis or cytotoxic activity in vitro or in vivo will increase the production of cytokines such as IFN-γ, GM-CSF, and TNF-α by the cells having phagocytosis or cytotoxic activity. The pharmaceutical preparation according to the present invention may be therefore used for the above purposes as well. In vitro, for example, the addition of the diabody-type bispecific antibody to a culture system comprising the above two kinds of the cells will increase the production of the cytokines.

An effective amount of the active ingredient may be optionally determined by those skilled in the art depending on the purpose of treatment, medical conditions of a patient to be treated such as kind, site or size of tumor, and administration route. A typical dose or daily dose may be first determined in vitro by using an assay method of growth or existence of the tumors known in the art, then determined with use of such an appropriate animal model as to allow extrapolation of the resulting dose range to human patients.

The pharmaceutical preparation of the present invention may optionally comprise various kinds of pharmaceutically acceptable components known in the art such as carrier, excipient, buffer, stabilizing agent and the like, depending on various factors such as the kind of the active ingredients, its formulation form, the route and purpose of administration, medical conditions of patient.

The pharmaceutical preparation of the present invention may be formulated into any form such as pill, liquid, powder, gel, air spray, microcapsule, and colloidal dispersion (liposome, micro emulsion, etc.).

The pharmaceutical preparation may be administered by injecting or infusing intraveneously, intraperitoneally, intracerebrally, intraspinally, intramuscularly, intraocularly, intraarterially, especially intrabiriarily, or via diseased tissue, or with use of a constant releasing agent system. The active ingredient according to the present invention may be administered through continuous fluid infusion or massive injection. The pharmaceutical preparation according to the present invention is preferably administered in combination with the cell having phagocytosis or cytotoxic activity. Alternatively, the active ingredient such as the diabody-type bispecific antibody may be mixed with the above cells so as to bind to them before its administration.

The constant releasing agent generally refers to a formulation that can release the active ingredient of the present invention for a certain period of time. One of the preferred constant releasing agents comprises a semi-permeable carrier of solid hydrophobic polymer such as protein, which is shaped into a form such as film or micro capsule.

The pharmaceutical preparation according to the present invention may be produced by a method that is optionally selected from, for example, "Guide Book of Japanese Pharmacopoeia", Ed. of Editorial Committee of Japanese Pharmacopoeia, Version No. 13, published Jul. 10, 1996 by Hirokawa publishing company The terms as used in the present specification and drawings are based on IUPAC-IUB Commission on Biochemical Nomenclature or on meanings of the terms conventionally used in the art.

The present invention will be explained more in detail by referring to the Examples, which are provided only for describing the specific embodiments of the present invention, but not for limiting the scope of the present invention. It is therefore to be understood that various embodiments based on the inventive concept of the present specification may be practiced within the scope of the present invention.

The following examples were or can be carried out with standard techniques well known to those skilled in the art unless otherwise described. Thus, unless otherwise described, specific procedures and treating conditions are in accordance with J. Sambrook, E. F. Fritsch & T. Maniatis, "Molecular Cloning", 2nd ed., Cold Spring Harbor Laboratory, Cold Spring Harbor, N.Y. (1989) and D. M. Glover et al. ed., "DNA Cloning", 2nd ed., Vol. 1 to 4, (The Practical Approach Series), IRL Press, Oxford University Press (1995) (DNA cloning), and with H. A. Erlich ed., PCR Technology, Stockton Press, 1989; D. M. Glover et al. ed., "DNA Cloning", 2nd ed., Vol. 1, (The Practical Approach Series), IRL Press, Oxford University Press (1995) and M. A. Innis et al. ed., "PCR Protocols", Academic Press, New York (1990) (PCR). A commercially available agent and kit were used in accordance with protocols attached thereto.

EXAMPLES

Example 1

Cloning of Anti-Epidermal Growth Factor Receptor Antibody

Mouse B cell hybridoma 528 producing anti-EGFR antibody was provided by Cell Resource Center for Biomedical Research, Institute of Development, Aging and Cancer, TOHOKU University. mRNA was extracted with ISOGEN (Nippon Gene Co.) and then cDNA was prepared by means of First-Strand cDNA Synthesis Kit (Amersham Biosciences Co.). PCR reaction was done for the cDNA using cloning primers that were synthesized based on Reference 1 to determine the sequences of variable regions of 528, VH (referred to as "5H") and VL (referred to as "5L")(FIG. 1).

Reference 1: Krebber, A. et al. Reliable cloning of functional antibody variable domains from hybridomas and spleen cell repertoires employing a reengineered phage display system. J Immunol Methods 201, 35-55. (1997).

Example 2

Preparation of Ex3 Diabody-expressing Vector

A representative example of the diabody-type bispecific antibody according to the present invention, Ex3 diabody (referred to as "Ex3"), consists of two molecules, i.e., "5HOL" and "OH5L." The expression vector was prepared based on the expression vector for Mx3 diabody (referred to as "Mx3") that was already constructed by the inventors and has specificity to MUC1 and CD3 (PCT Publication No. WO02/06486). Thus, "5H" was amplified with PCR using A-B primers comprising a restriction enzyme site, digested with NcoI-EagI, and was replaced with "MH" in pSNE4-MHOL (VH of anti-MUC1 antibody (MUSE11) (referred to as "MH")—GGGGS (referred to as "G1")—VL of anti-CD3 antibody OKT3 (referred to as "OL") to give pRA-5HOL. Similarly, "5L" was amplified with PCR using C-D primers comprising a restriction enzyme site, digested with EcoRV-SacII, and was replaced with "ML" in pSNE4-OHML (VH of OKT3 (referred to as "OH")—"G1"—VL of MUSE11 (referred to as "ML") to give pRA-OH5L (FIG. 2). A c-myc peptide tag for detection and a His-tag (Hisx6:histidine-hexamer) for purification were introduced successively into the vectors.

```
A NcoI-5H back primer              [SEQ ID No.1]
5'-nnnccatggcccaggtccagctgcagcagtctg-3'

B 5H-EagI forward primer           [SEQ ID No.2]
5'-nnncggccgaggagactgtgagagtggt-3'
```

```
                        -continued
C EcoRV-5L back primer              [SEQ ID No.3]
5'-nnngatatcctaatgacccaatctcc-3'

D 5L- SacII forward primer          [SEQ ID No.4]
5'-nnnccgcggcacgtttgatttccagcttg-3'
```

Example 3

Expression of "5HOL" and "OH5L" by *E. coli*

Each *E. coli* BL21 strain (E3) was transformed with the expression vector pRA-5HOL and pRA-OH5L, respectively, and cultured in 2×YT medium at 28° C. When O.D.$_{600}$ reached about 0.8, expression was induced by the addition of IPTG to a final concentration of 1 mM and cultured overnight under shaking. The resulting bacteria were separated from culture supernatant by centrifugation, crushed with ultrasonic wave and subjected again to centrifugation to obtain supernatant as a soluble fraction within the bacteria cell and precipitate as an insoluble fraction within the bacteria cell. Since SDS-PAGE and Western-blotting of each fraction revealed that almost all of the "5HOL" and "OH5L" was contained in the insoluble fraction within the bacteria cell, these proteins were then prepared from said insoluble fraction (FIG. 3, lanes 1 & 5: culture supernatant; lanes 2 & 6: soluble fraction within the bacteria cell; lanes 3 & 7: insoluble fraction within the bacteria cell; lane 4: after purification and refolding).

Example 4

Purification and Refolding of "5HOL" and "OH5L"

After being solubilized by soaking the insoluble fraction within the bacteria cell into 6 M guanidine hydrochloride/PBS overnight at 4° C., the proteins were purified by means of metal-chelate affinity chromatography using a metal-chelate resin (TALON™: CLONTECH Co.) having specificity to His-Tag in a denatured state. Yield of each protein after the purification was about 5 mg per 1 L of culture medium of the transformed cells, respectively.

Figure 3:
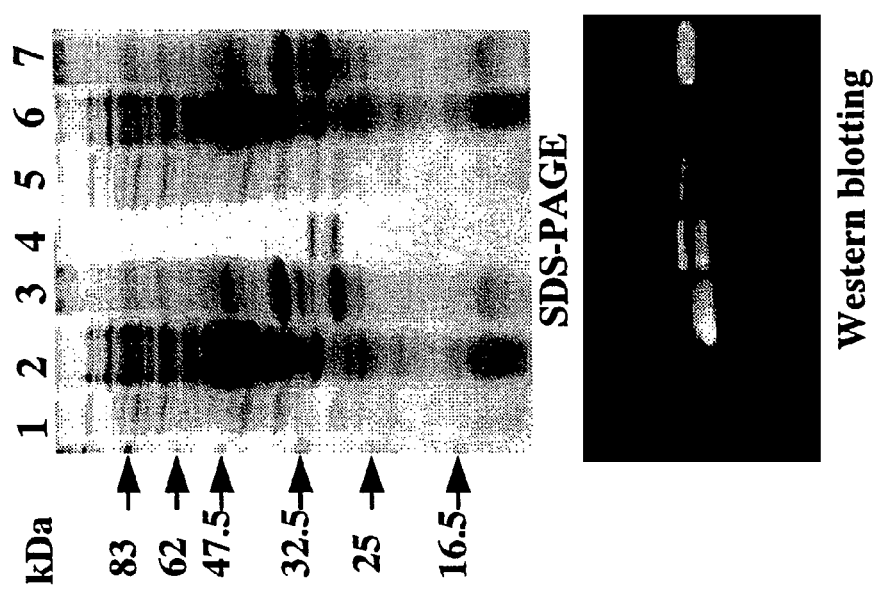
FIG. 3 shows photos of SDS-PAGE (upper) and Western-blotting (lower) showing the expression of 5HOL and OH5L in E. coli strain BL21.
Figure 4:
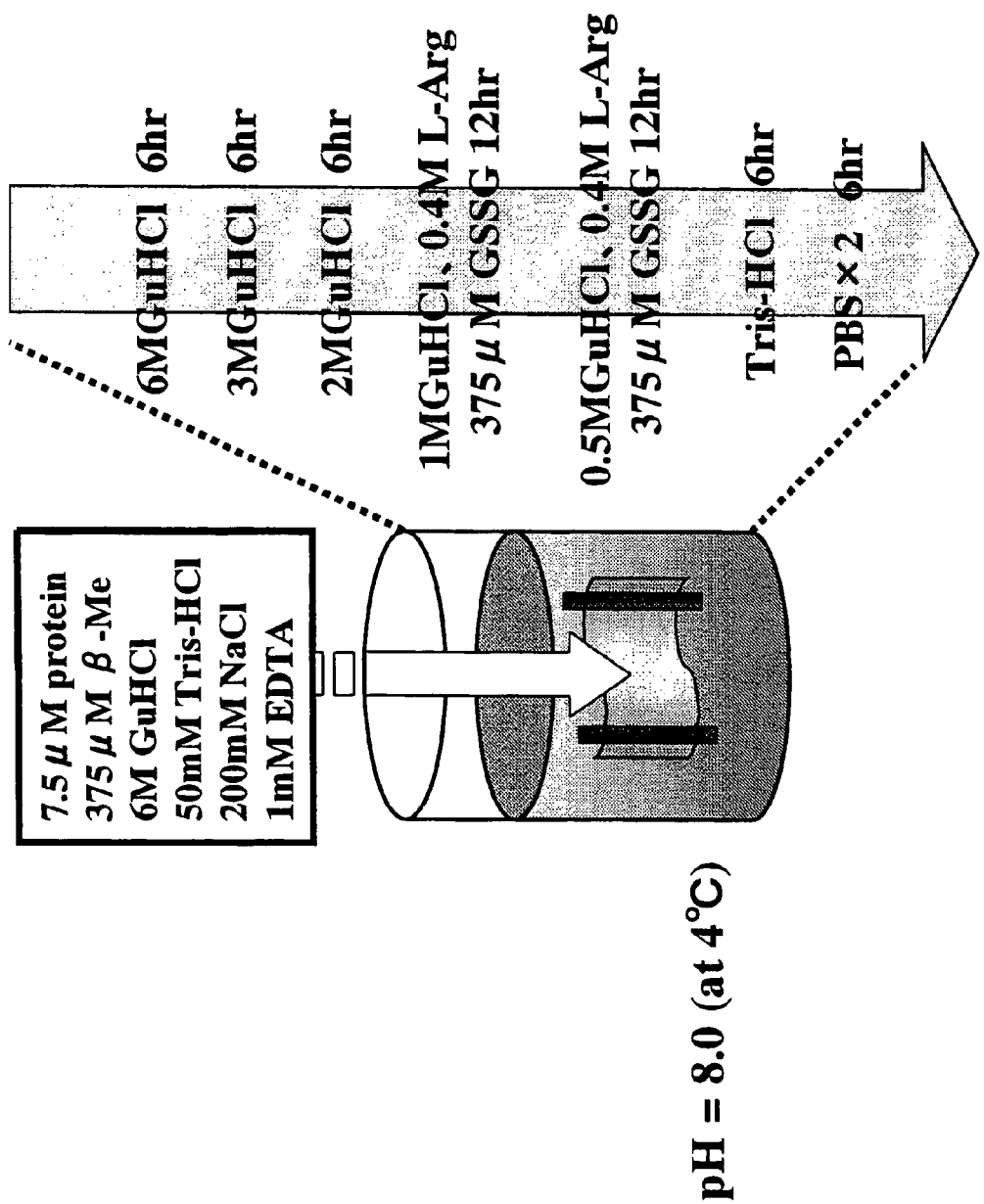
FIG. 4 shows steps of refolding by step-by-step dialysis.

Since the thus purified proteins were in the denatured state due to guanidine hydrochloride, it was necessary to refold them in order to obtain a three-dimensional structure maintaining the activity. After being diluted to 7.5 μM, both the "5HOL" and "OH5L" proteins in the same quantity were mixed together (the total protein concentration: 7.5 μM and Ex3 concentration: 3.75 μM). 2-mercaptoethnaol (β-Me) in a 50-fold amount of the total proteins was then added to a final concentration of 375 μM, and the proteins were kept standing still for 4 hours at 4° C. for a reductive reaction. After the reaction sample was put into a dialysis membrane, it was subjected to step-by-step (or gradual) dialysis for removing the denaturing agent by gradually reducing the concentration of guanidine hydrochloride in an outer liquid, i.e., 3 M (6 hr), 2 M (6 hr), 1 M (12 hr), 0.5 M (12 hr) and 0 M. At the stage of the concentration of 1 M and 0.5 M during the step-by-step dialysis, an oxidant of oxidized glutathione (GSSG) and an anti-coagulant of L-arginine (L-Arg) were added in the outer liquid to a final concentration of 375 μM and 0.4 M, respectively and the reaction mixture was kept at 4° C. for promoting oxidization (FIG. 4). The efficiency of refolding was about 30%. SDS-PAGE of the Ex3 obtained by the purification and the mixture of the same quantity of the "5HOL" and "OH5L" followed by refolding confirmed that they were purified with a very high degree and they had formed a homogeneous hetero-dimer (FIG. 3).

Example 5

Evaluation of Ex3 (1)—Flow Cytometric Analysis

The binding activity of Ex3 to various cells was examined with Flow cytometry. Target cells were mixed with a first antibody of Ex3 of 100 μL, left to stand still for 30 min. at 4° C., washed twice with 0.1% NaN$_3$/PBS, mixed with a second antibody of anti-c-myc antibody followed by the same procedures, and finally mixed with a third antibody of FITC-labeled anti-mouse antibody followed by the same procedures, and subjected to the detection of fluorescence. For a negative control, only the procedures after the addition of the second antibody were repeated. On the other hand, OKT3 IgG and 528 IgG were used for a positive control (referred to as "PC") in T-LAK cell and TFK-1 cell (human bile duct carcinoma cell line), respectively. The results showed that Ex3 could bind to both the cells (FIG. 5, upper).

Figure 5:
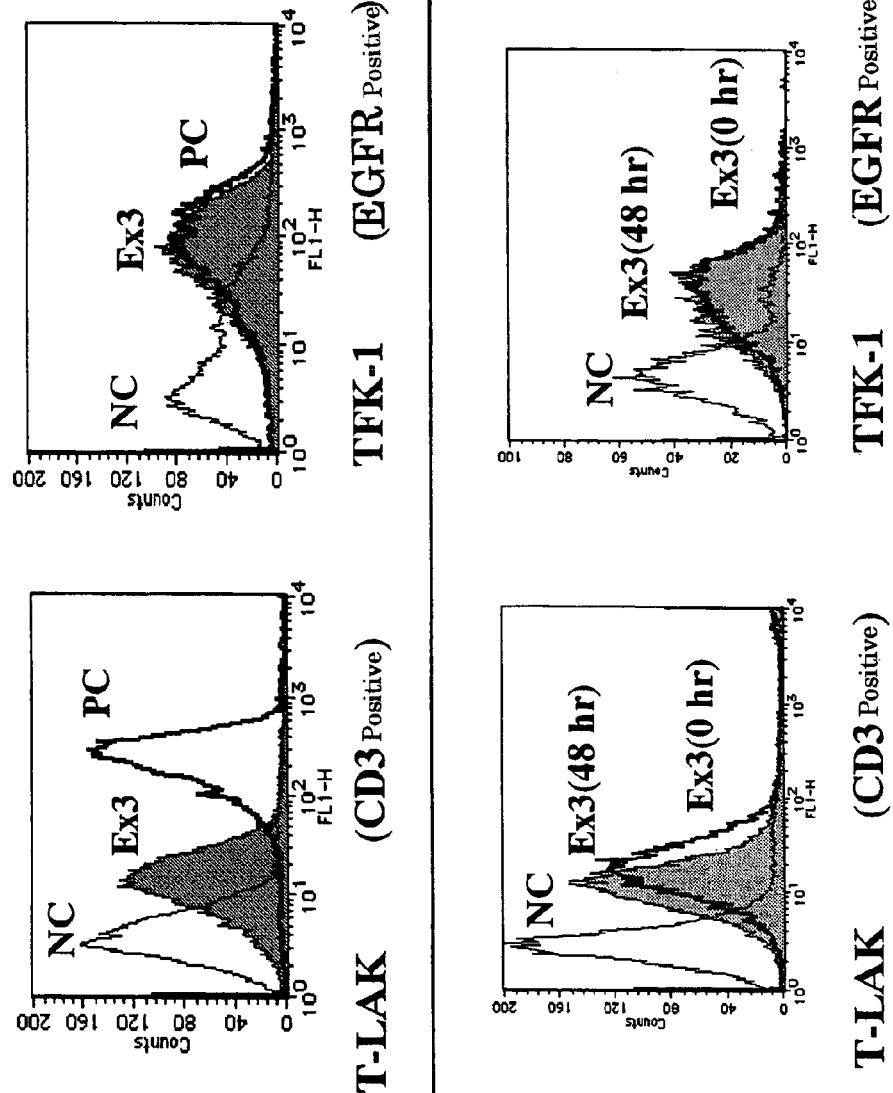
FIG. 5 shows the results of binding activity of Ex3 to various cells by Flow Cytometry.

Stability was examined by still standing for 48 hours under physiological conditions (37° C., RPMI 1640 medium) followed by the same procedures to confirm that there was no substantial change in the binding activity (FIG. 5, lower).

In order to examine whether or not the recognition site of Ex3 was the same as that of each parent antibody, the same procedures as in the case of PC were repeated after the addition of Ex3 (20 μg), and inhibition of the parent antibodies of OKT3 IgG (0.1 μg) and 528 IgG (0.25 μg) was examined. The results showed that binding ability of the parent antibodies was decreased, indicating that the recognition sites of Ex3 and its parent antibodies were the same with each other (FIG. 6, the left (OKT3 IgG) and the right (528 IgG)).

Figure 7:
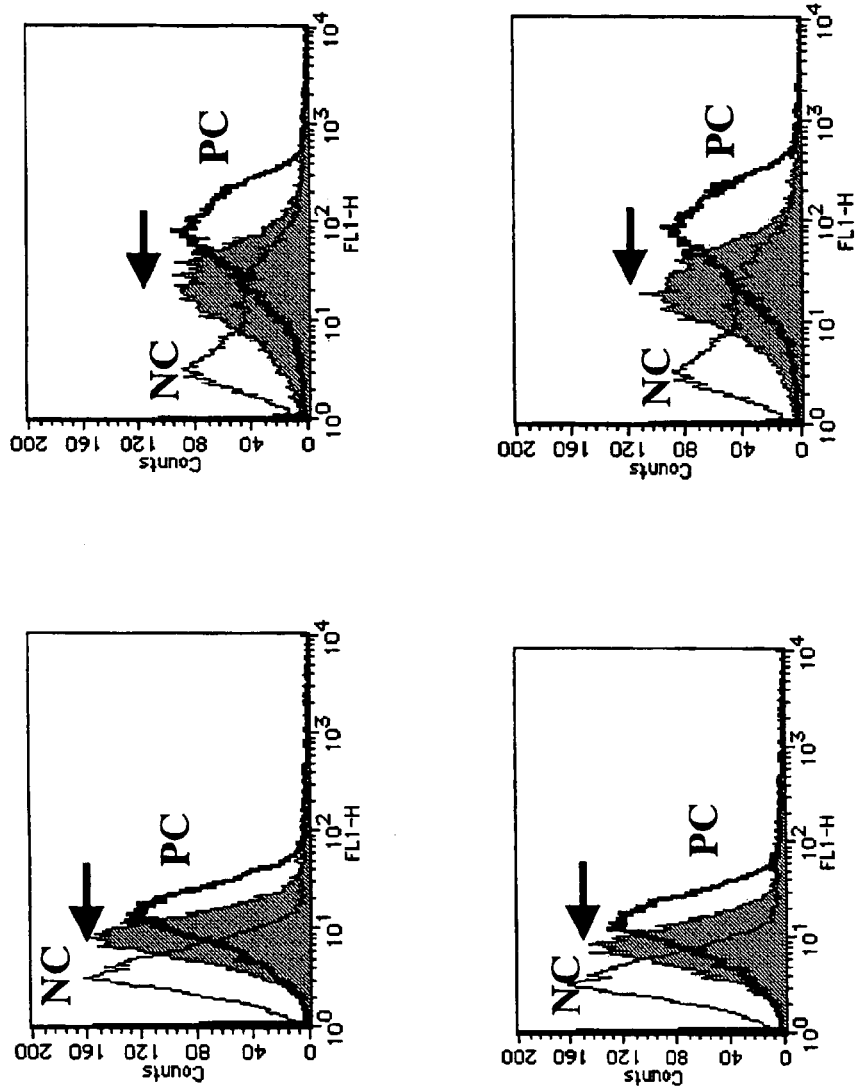
FIG. 7 shows the results of absorption test of Ex3 by Flow Cytometry.

Absorption test, in which after the reaction of Ex3 with an excess amount of T-LAK cell (upper, 5×10$^6$) or TFK-1 cell (lower, 5×10$^6$), each cell was treated with the resulting supernatant and subjected to Flow cytometry, showed that the binding ability was decreased in any combination. These results indicated that a single Ex3 molecule bound to both the cells, i.e., Ex3 had bispecificity (FIG. 7).

Example 6

Evaluation of Ex3 (2)—Microscopic Observation

Figure 8:
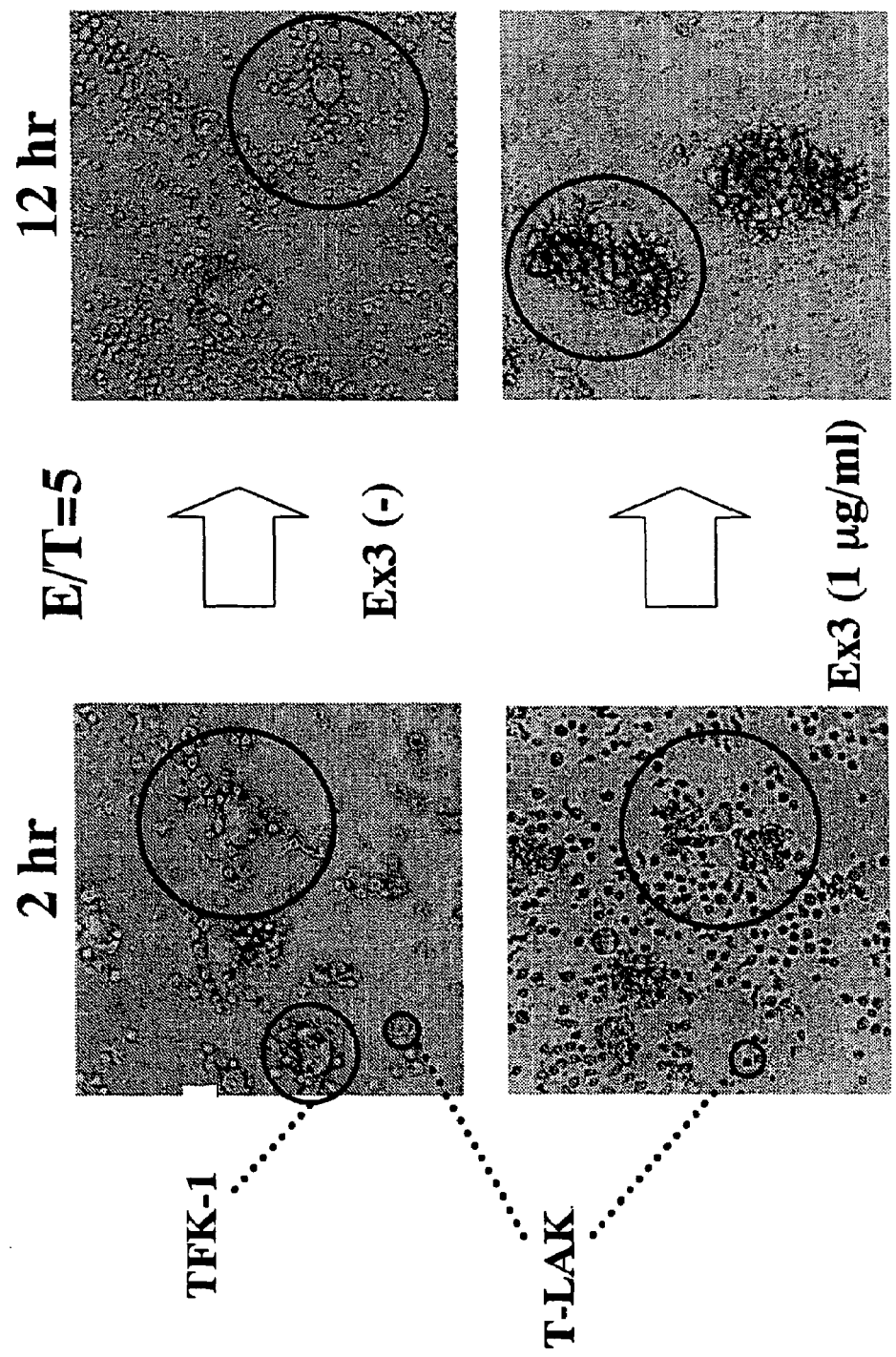
FIG. 8 are microscopic photos showing the accumulation of T-LAK cells around TFK-1 cells by Ex3.

After cancers cells were cultured overnight while being attached, they were mixed with T-LAK cells alone or in combination with Ex3, and microscopically observed in time course. While substantial no change was observed even after 12 hours in the case of the addition of T-LAK cells alone, T-LAK cells started to accumulate around the cancer cells after 2 hours and almost all of them was accumulated around the cancer cells after 12 hours in a plate wherein Ex3 was mixed in addition to T-LAK cells (FIG. 8). The term "E/T" or "Effector/Target" as used in a drawing attached to the present specification means the ratio of "effector (T-LAK cell)/target (TFK-1 cell)."

Further, in an inhibition test, while plates to which the parent antibody OKT3 or 528 IgG was added showed almost no accumulation of the T-LAK cells after 18 hours, plates to which OKT8 (anti-CD8 antibody) or MUSE11 (anti-MUC1 antibody) IgG having no relevance to the system showed almost the same accumulation as in the case of not being added (FIG. 9).

Example 7

Evaluation of Ex3 (3)—In Vitro Cytotoxicity Test (MTS Assay)

Figure 10:
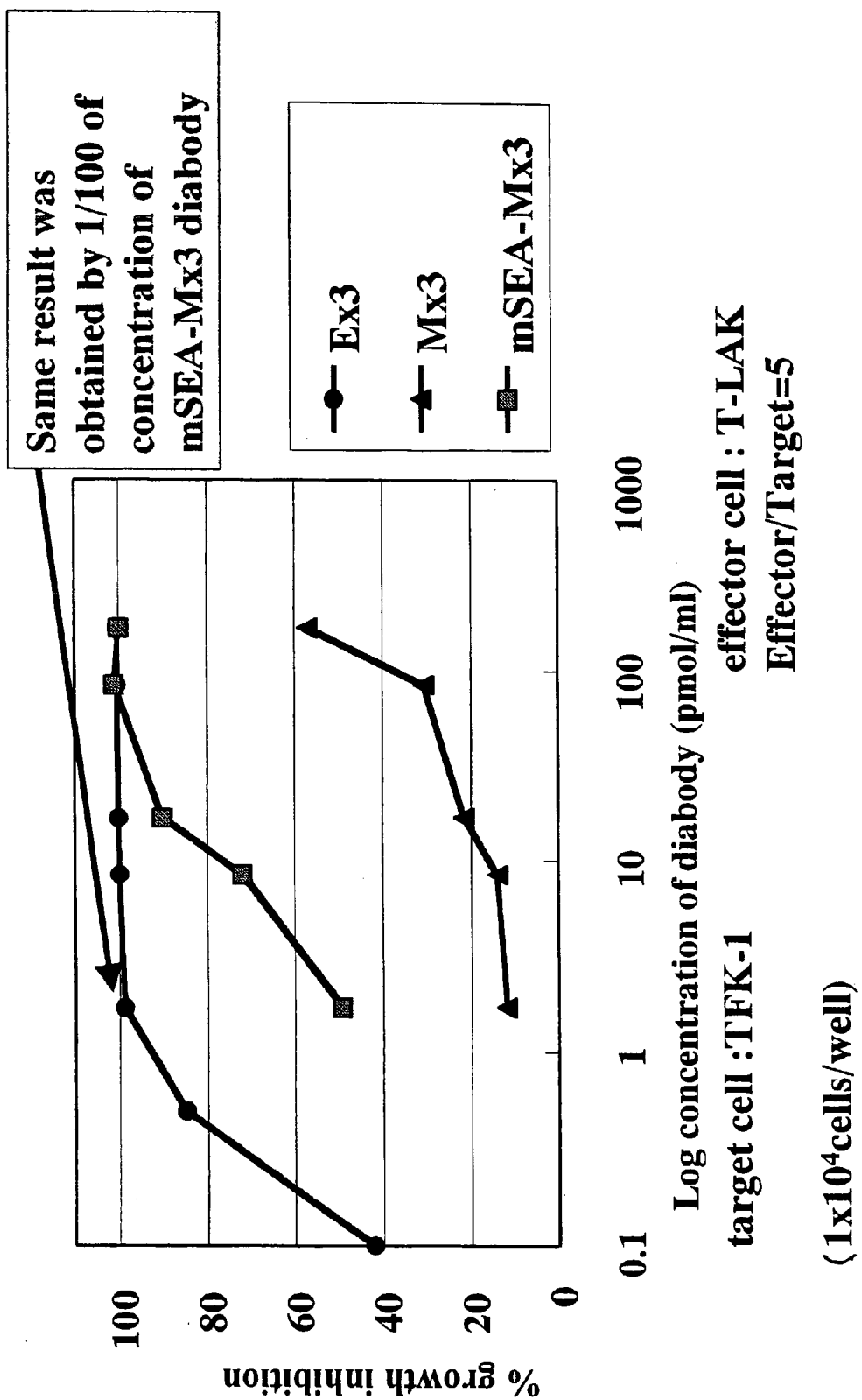
FIG. 10 shows the results of in vitro cytotoxicity test (MTS assay) by various diabody-type bispecific antibody such as Ex3.
Figure 11:
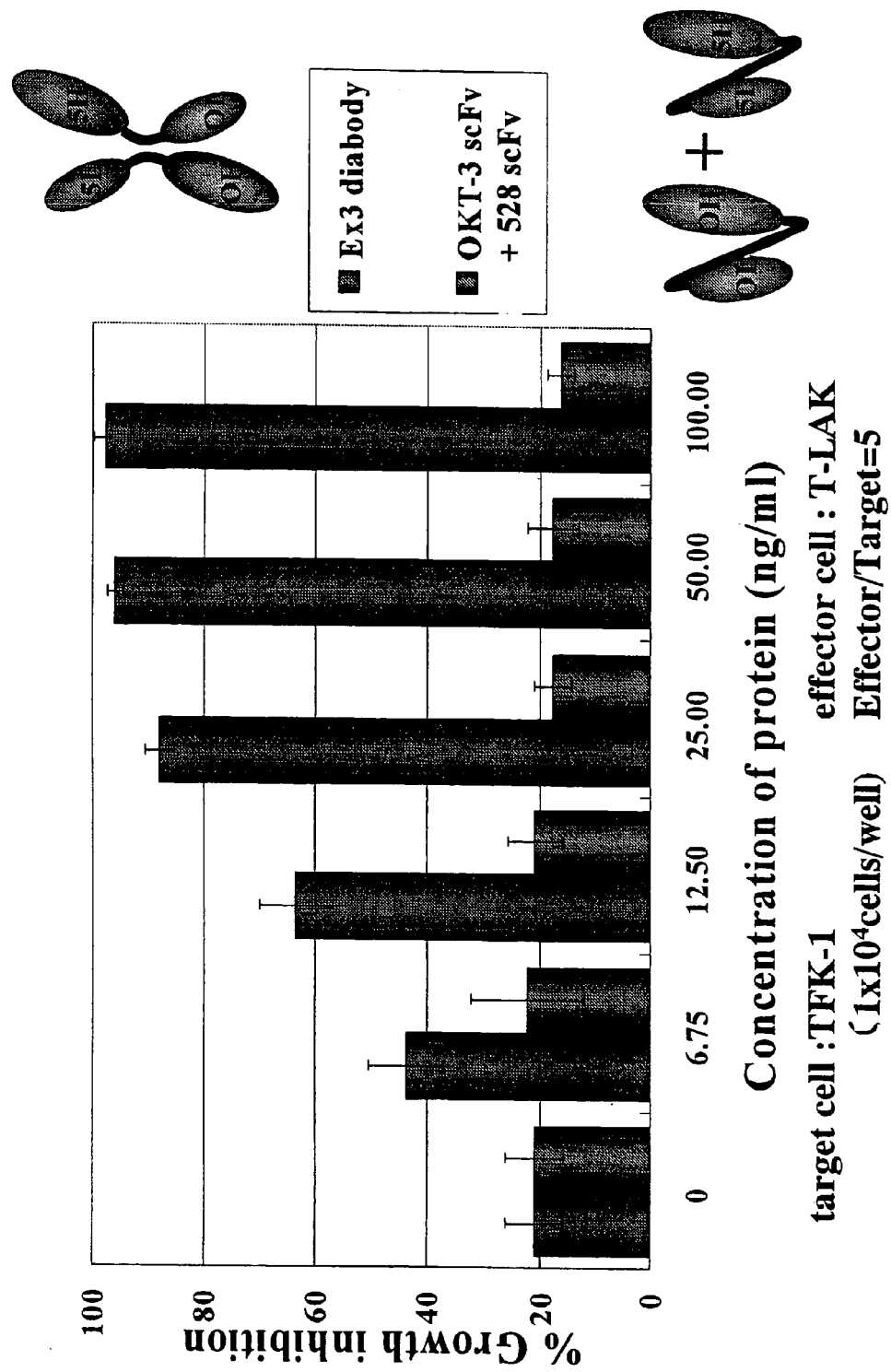
FIG. 11 shows comparison of in vitro cytotoxicity between Ex3 (left bar) and the mixture of each scFv (right bar).
Figure 12:
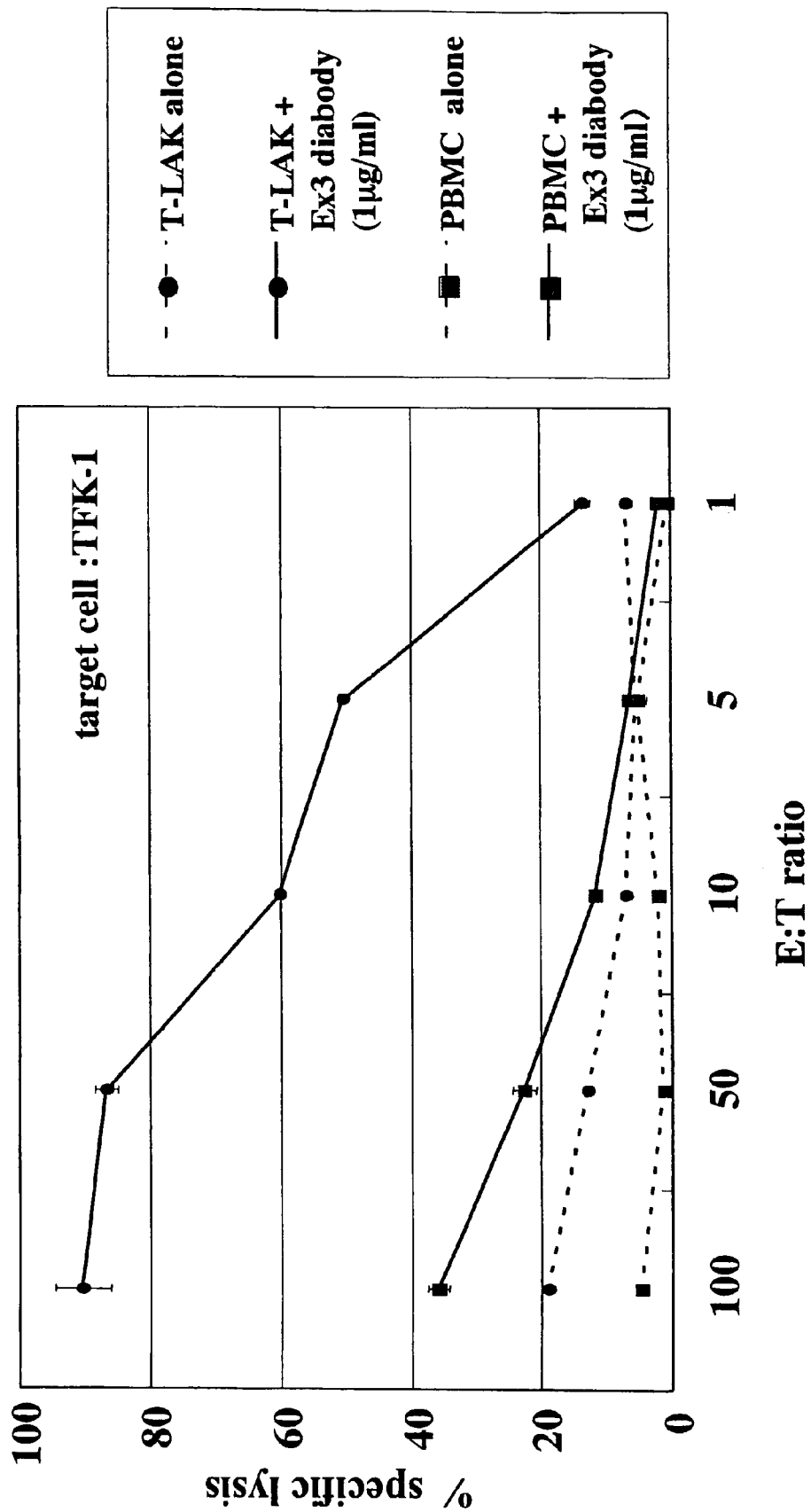
FIG. 12 shows the results of in vitro cytotoxicity test ($^{51}$Cr release assay) by the diabody-type bispecific antibody Ex3.

The degree of damage in TFK-1 cell due to T-LAK cell was determined by MTS assay. TFK-1 cell sample was adjusted to contain $10^4$ cells per 100 μL of RPMI 1640 by counting the cell, and its aliquot of 100 μL was dispensed into each well of a 96-well plate to stand still overnight at 37° C. After being diluted with RPMI to a desired concentration of the protein according to the present invention, 50 μL of which was put into each well of the above plate. LAK cell was diluted with RPMI to a desired E/T ratio, and 50 μL o which was put into each well of the above plate as well. After being cultured for 48 hours at 37° C., the cells were removed from culture medium, washed with PBS, mixed with MTS (CellTiter 96 AQueous Non-Radioactive Cell Proliferation Assay, Promega Co.), PMS (CellTiter 96 AQueous Non-Radioactive Cell Proliferation Assay, Promega Co.), and RPMI, and incubated for 30-60 min. at 37° C., followed by the detection of absorbance at 490 nm with a plate reader. It was observed that Ex3 showed much stronger effects than Mx3 or mSEA-Mx3. The concentration of Ex3 required to kill 100% of TFK-1 cells was as low as 1 pmol/mL (ca. 60 ng/mL), which was about 100 times lower than that of mSEA-Mx3 (FIG. 10).

On the other hand, an equimolar mixture of OKT3 scFv and 528 scFv did not show any cyotoxie effect even at a high concentration. These results showed that it was important to physically bridge lymphocytes and cancer cells, i.e., to get them close together by the bispecific antibody in addition to the effects by each antibody per se, i.e., the activation of T-LAK through the stimulation of CD3 by OKT3, and growth inhibition of TFK-1 due to the blocking of EGFR by 528, Example 8

Evaluation of Ex3 (4)—In Vitro Cytotoxicity Test ($^{51}$Cr Release Assay)

Although MTS assay could easily examine the cytotoxicity in vitro, it detected only growth inhibition of the attached cancer cells. $^{51}$Cr release assay was then carried out, which could detect directly the cytotoxicity. The results showed a significant cytotoxicity due to the addition of Ex3, which would increase depending on the increase of the E/T ratio. PBMC (peripheral blood mononuclear cell) would be used instead of the lymphocytes that have activated ex vivo such as T-LAK cell in an adoptive immunotherapy. The increase of the cytotoxicity was also observed depending on the increase of the E/T ratio even with the use of PBMC as an effector cell.

Figure 13:
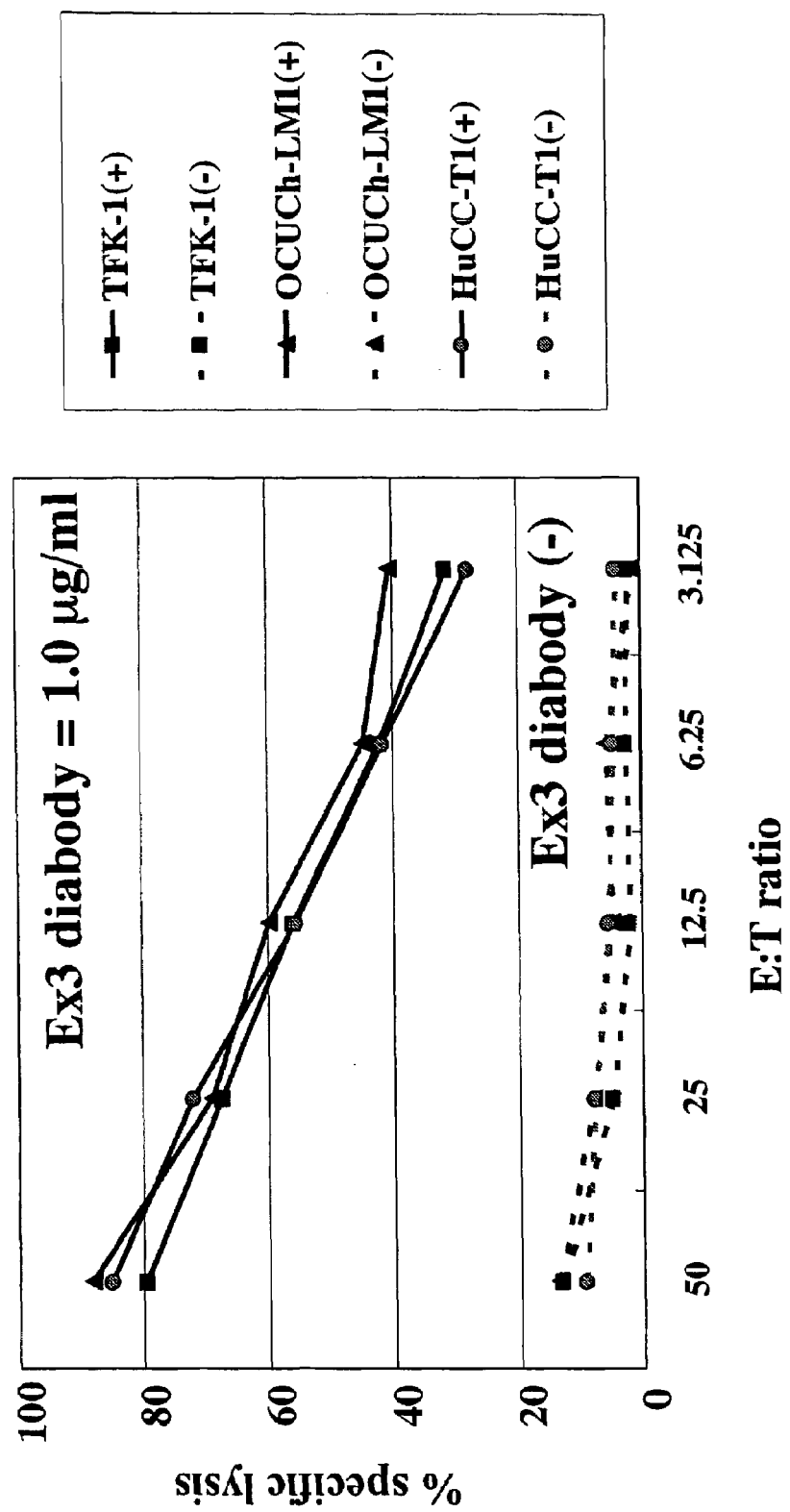
FIG. 13 shows the results of in vitro cytotoxicity test ($^{51}$Cr release assay) on various cells by the diabody-type bispecific antibody Ex3.

The increase of the cytotoxicity due to the existence of Ex3 depending on the increase of the E/T ratio was observed for other EGFR (Her1)-positive bile duct carcinoma cells as well (FIG. 13). On the other hand, the addition of Ex3 did not increase the cytotoxicity of T-LAK cell for EGFR (Her1)-negative cells (Table 1).

Figure 14:
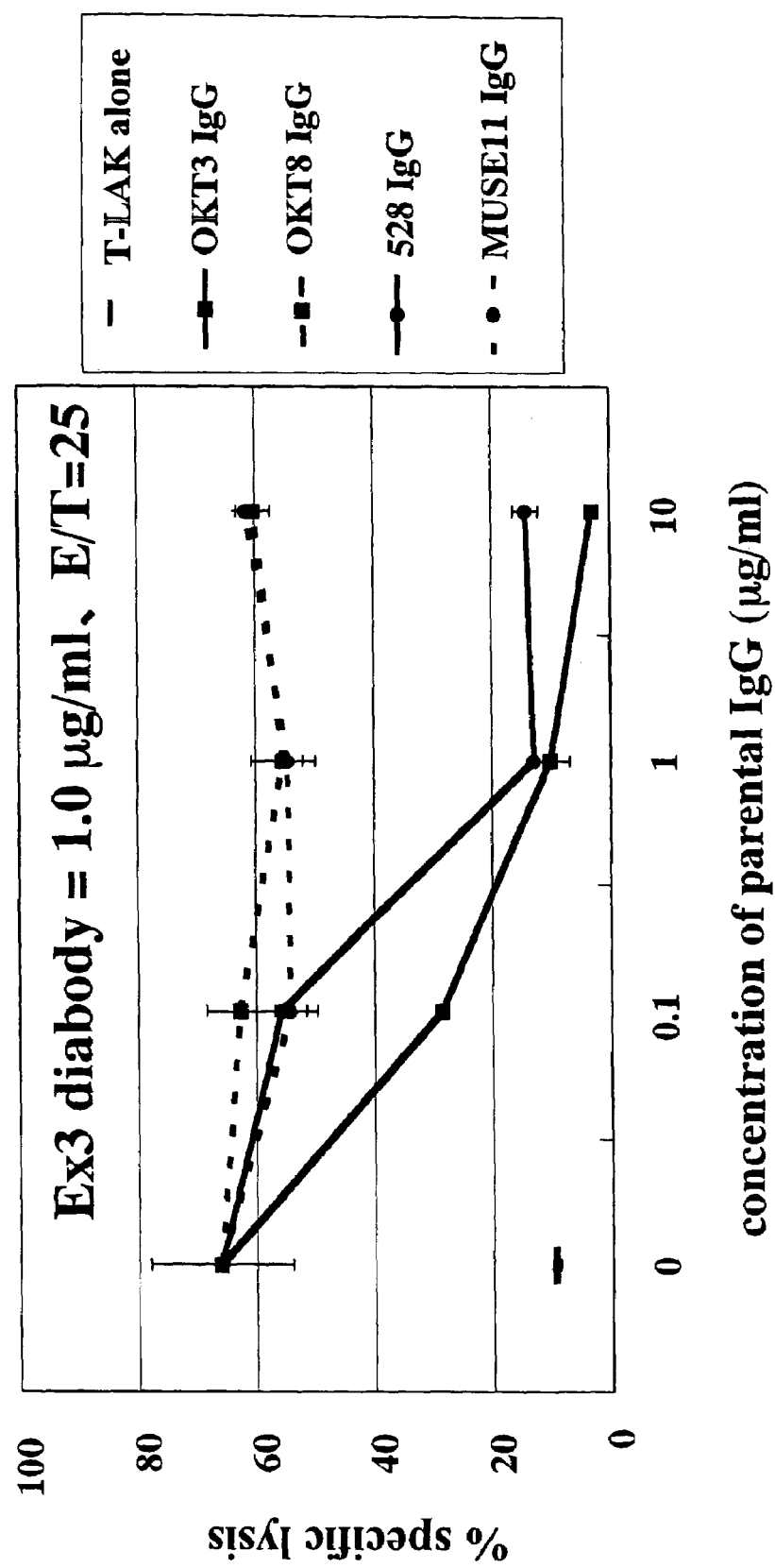
FIG. 14 shows the results of inhibition test by the addition of IgG.

Further, in an inhibition test, while the addition of the parent antibodies OKT3 or 528 IgG showed the decrease of cytotoxicity, the addition of OKT8 or MUSE11 IgG that had no relevance to the system did not show any (FIG. 14).

The abbreviations for the terms used in Table 1 and drawings are as follows.

| | |
|---|---|
| TFK-1: | human bile duct adenocarcinoma; |
| OCUCh-LM1: | human bile duct carcinoma; |
| HuCC-T1: | human bile duct carcinoma; |
| OBA-LK1: | human lung large cell carcinoma; |
| A549: | human lung adenocarcinoma; |
| CRL1500: | human breast carcinoma; |
| SK-BR-3: | human breast adenocarcinoma; |
| A431: | human epidermoid carcinoma; |
| MCF-7: | human breast adenocarcinoma; |
| NCI-H69: | human lung small cell carcinoma; |
| CHO: | Chinese hamster ovarian cell. |

TABLE 1

6 hr $^{51}$Cr release assay (E/T = 25)

| target cells | T-LAK alone (A) | Ex3 diabody 1 μg/ml (B) | enhancement of cytotoxicity (B/A) | origin |
|---|---|---|---|---|
| EGFR positive | | | | |
| TFK-1 | 29.00 ± 0.86 | 76.39 ± 0.86 | 2.64 ± 0.04**** | bile duct |
| OCUCh-LM1 | 21.93 ± 0.57 | 64.96 ± 0.33 | 2.96 ± 0.04**** | bile duct |
| HuCC-T1 | 15.15 ± 0.79 | 63.78 ± 0.30 | 4.23 ± 0.11**** | bile duct |
| OBA-LK | 44.09 ± 0.75 | 87.11 ± 2.26 | 1.98 ± 0.03**** | lung (large cell carcinoma) |
| A549 | 14.15 ± 2.61 | 66.84 ± 4.68 | 5.14 ± 0.60*** | lung (adenocarcinoma) |
| CRL1500 | 8.91 ± 1.07 | 45.23 ± 2.90 | 5.22 ± 0.35*** | breast |
| SK-BR-3 | 39.92 ± 1.18 | 84.18 ± 8.06 | 2.11 ± 0.11** | breast |
| A431 | 15.99 ± 1.99 | 81.23 ± 6.28 | 5.22 ± 0.36*** | epidermoid cancer |
| EGFR negative | | | | |
| MCF-7 | 16.83 ± 0.67 | 10.59 ± 0.35 | 0.62 ± 0.02** | breast |
| NCI-H69 | 54.95 ± 2.28 | 46.27 ± 4.53 | 0.84 ± 0.04 | lung (small cell carcinoma) other species |
| CHO-K1 | 42.92 ± 5.22 | 49.13 ± 2.41 | 1.18 ± 0.08 | chinese hamster ovarian cell |

**p < 0.01,
***p < 0.001,
****p < 0.0001

Example 9

Evaluation of Ex3 (5)—Secretion of Various Cytokines

Figure 15:
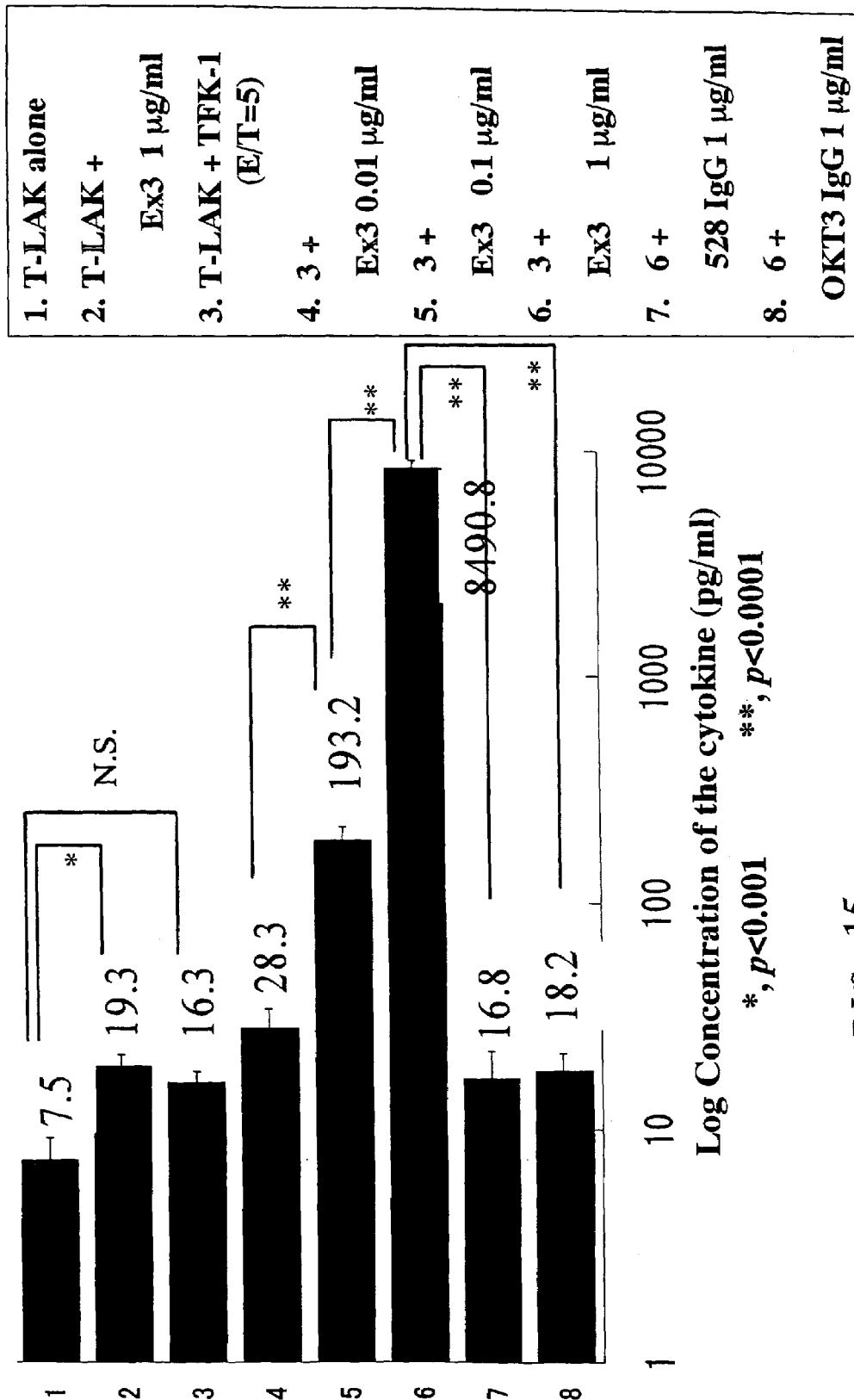
FIG. 15 shows increase of the production of IFN-γ by the addition of Ex3.

The production amounts of various cytokines were determined in order to identify a factor responsible for the increase of the cytotoxicity of T-LAK cell. TFK-1 cells were attached to a plate and left to stand still overnight, to which T-LAK cells alone and in combination of Ex3 with various concentrations were then added, followed by the detection of the amounts of cytokines in culture supernatant by means of ELISA kit (ENDOGEN Co.) after 48 hours. While no remarkable increase in IFN-γ production was observed in the plates to which T-LAK cell, T-LAK cell plus Ex3, or T-LAK cell plus TFK-1 cell were added, the increase in IFN-γ production was observed in a concentration-dependent manner by the addition of Ex3, T-LAK cell and TFK-1 cell. The addition of the parent antibody OKT3 or 528 IgG showed inhibition effect, but not induced the production of IFN-γ (FIG. 15).

Figure 16:
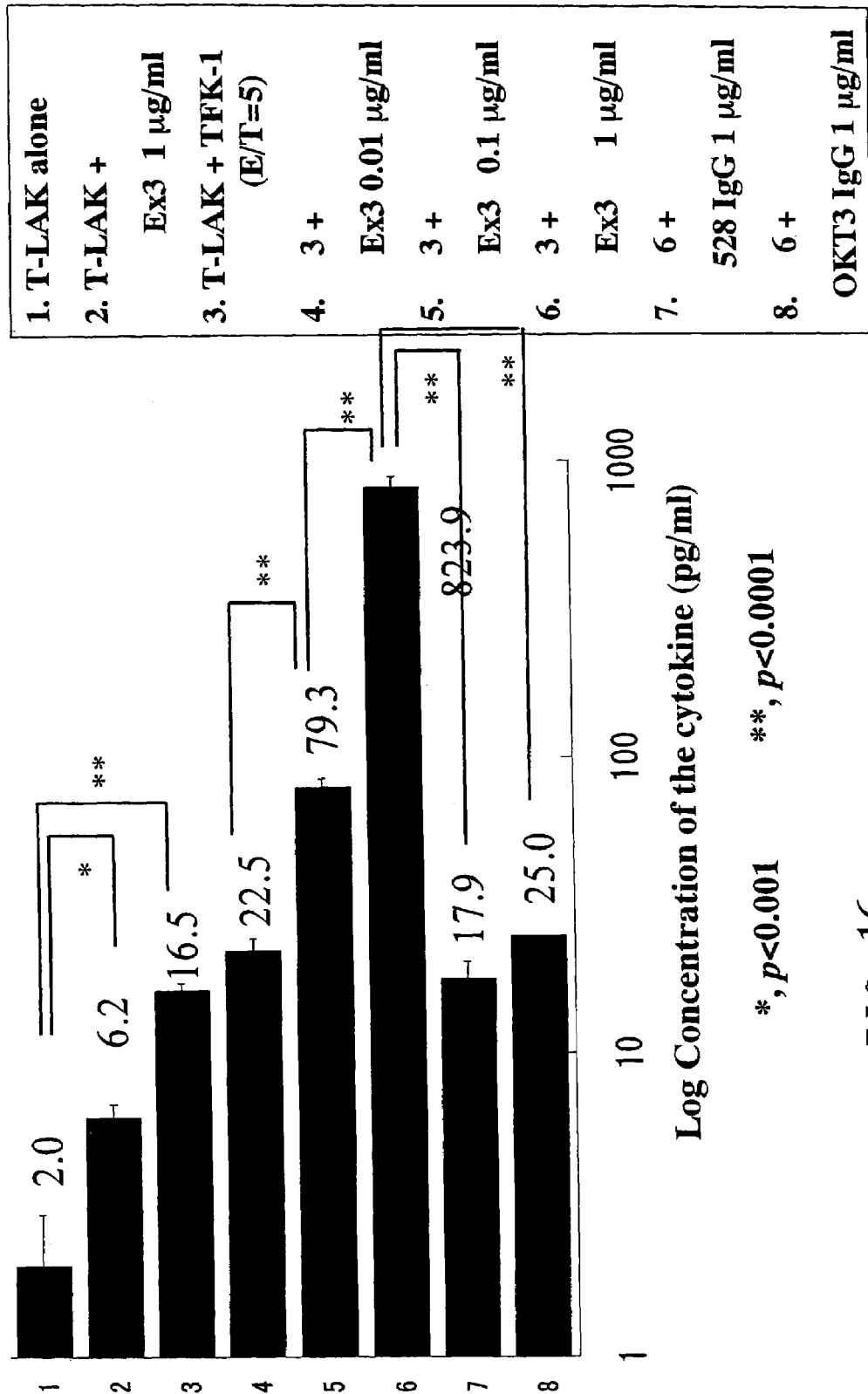
FIG. 16 shows increase of the production of GM-CSF by the addition of Ex3.
Figure 17:
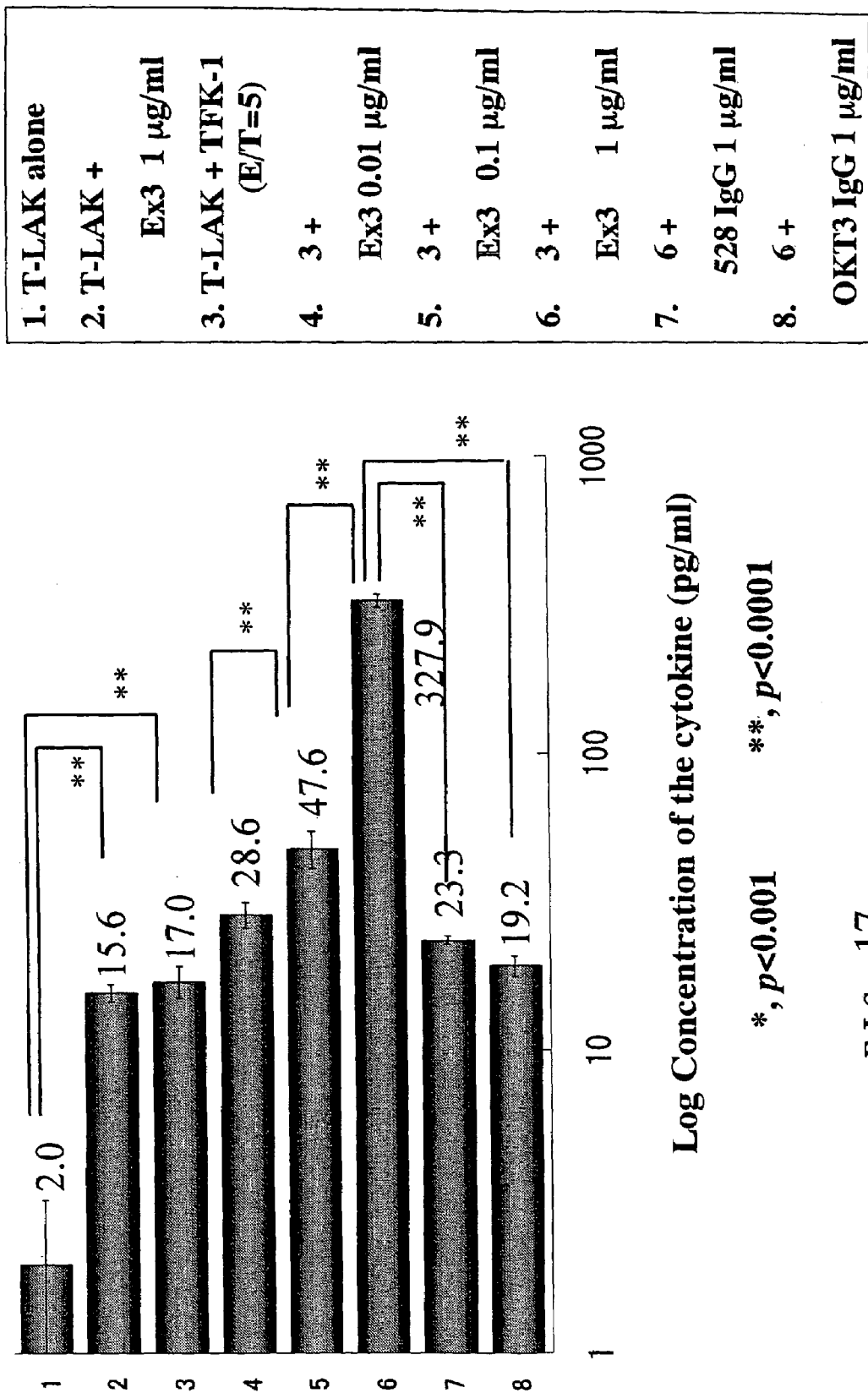
FIG. 17 shows increase of the production of TNF-α by the addition of Ex3.
Figure 18:
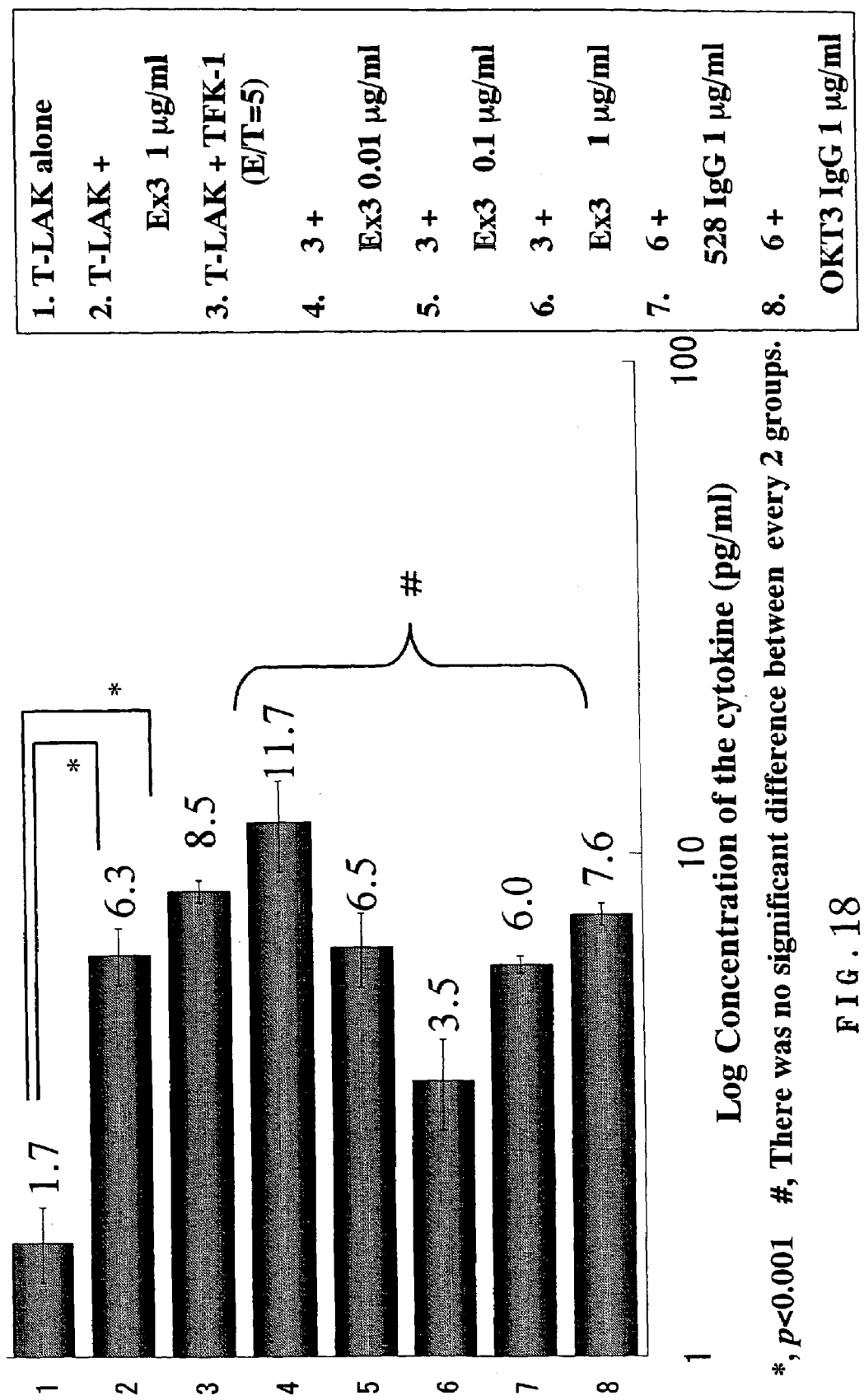
FIG. 18 shows change of the production of IL-2 by the addition of Ex3.

The similar results were obtained with respect to GM-CSF and TNF-α (FIGS. 16 & 17). However, there was not increase in the concentration-dependent manner, but a slight decrease in the production of IL-2 (FIG. 18).

Figure 19:
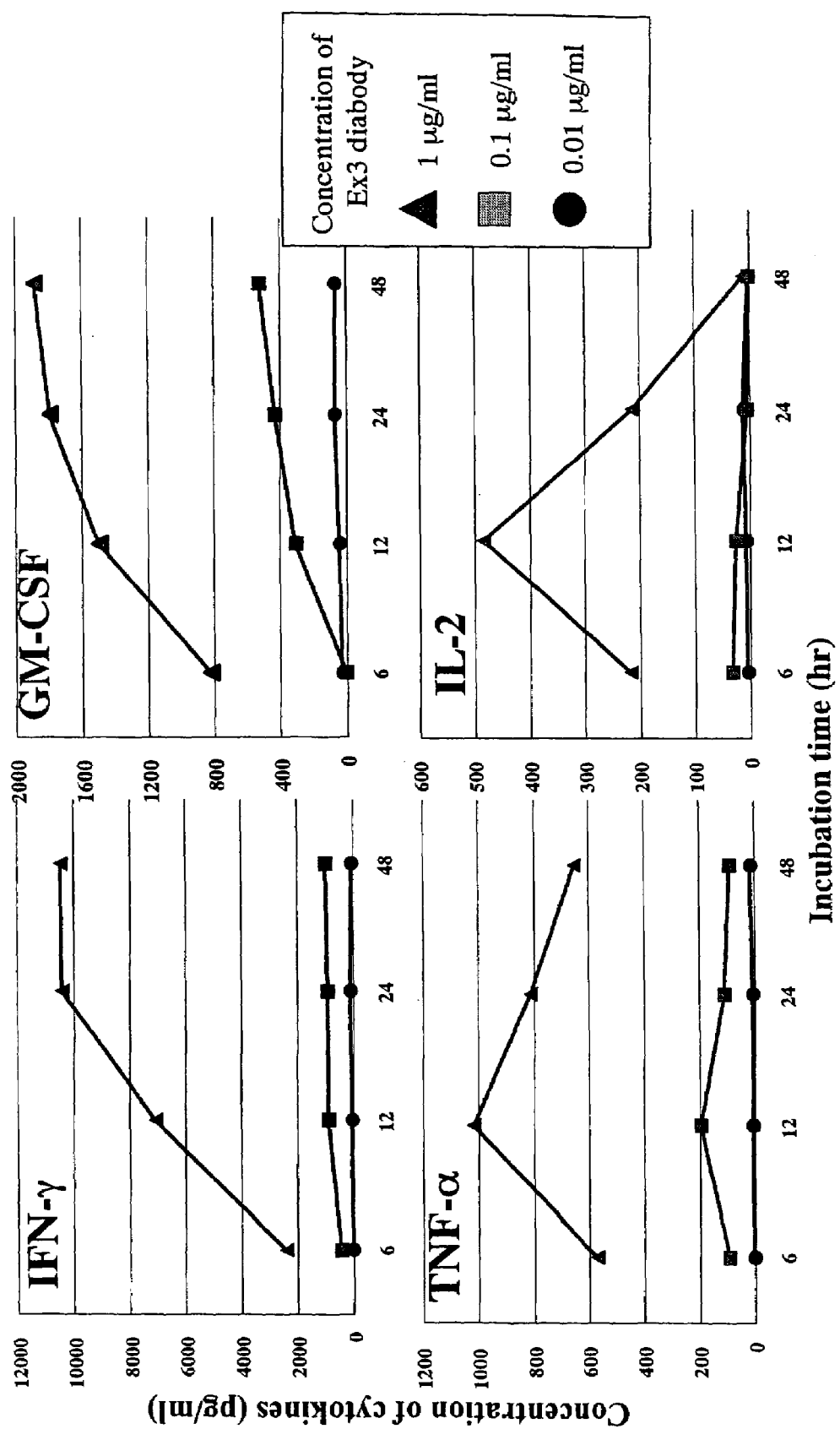
FIG. 19 shows time-course change of the production of cytokines.

Changes in time course in the production of various cytokines were determined by means of ELISA. While the production off IFN-γ and GM-CSF were increased in time course in the concentration-dependent manner, the production of TNF-α and IL-2 reached their highest levels in 12 hours and then decreased drastically. It was considered that the target cells, TFK-1, died 12 hours later, incorporated and digested by T-LAK cells without producing IL-2 and the like any more (FIG. 19). This assumption seems to coincide well with the results shown in FIG. 18.

Example 10

Evaluation of Ex3 (6)—In Vivo Cytotoxicity Test

SCID mice were injected subcutaneously with $5 \times 10^6$ of TFK-1 cells ten and several days after they had been taken. Ten days after the grafting of the TFK-1 cells (diameter of the tumor was about 4-6 mm), the mixture of $2 \times 10^7$ of T-LAK cells and each antibodies was injected intravenously at a tail of the mice for consecutive 4 days. The diameter of the tumor was measured every one week, and the volume of the tumor was estimated from its major axis and minor axis. This test was stopped when the diameter of the tumor in a control went beyond 20 mm.

Figure 20:
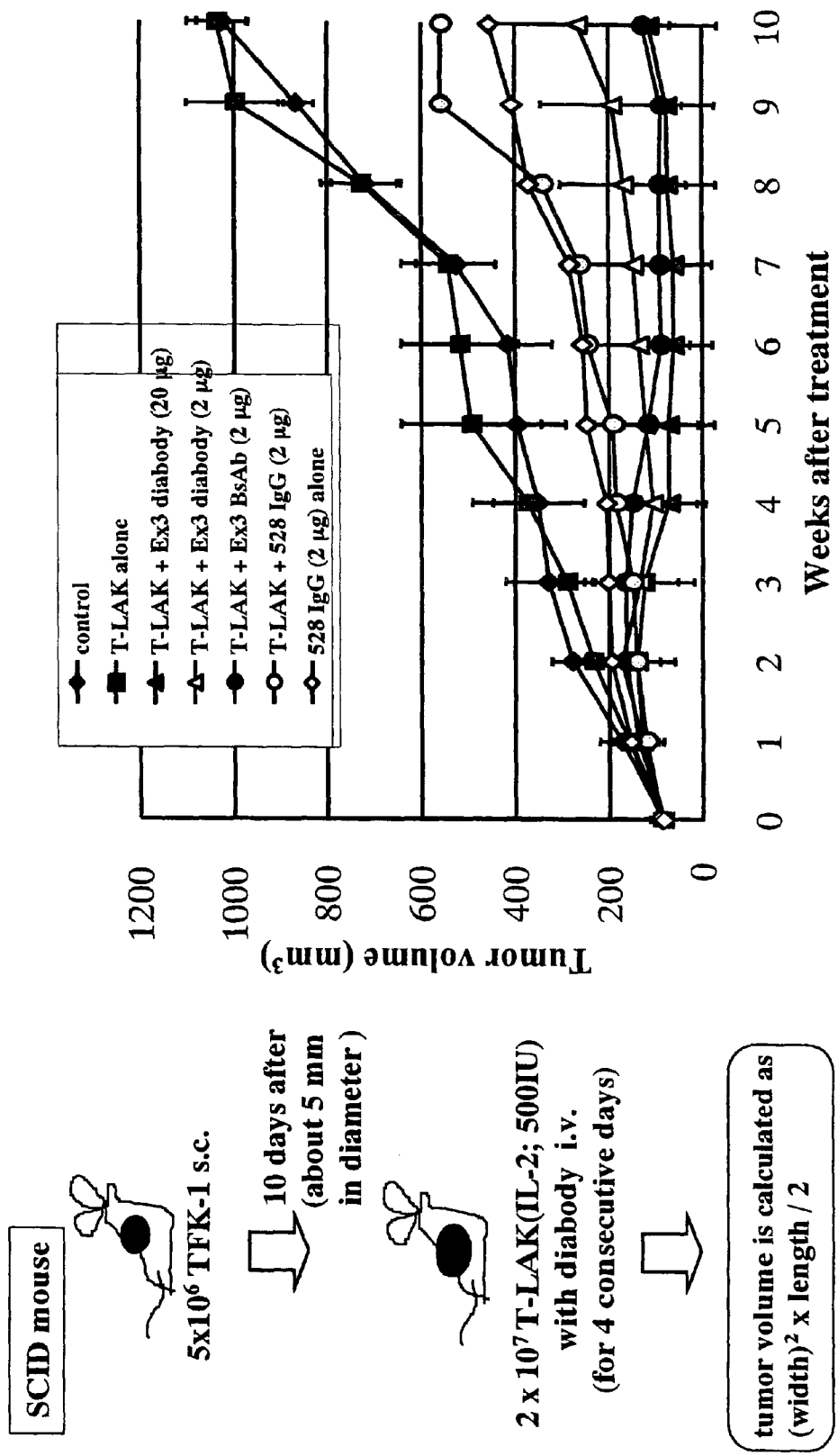
FIG. 20 shows the results of in vivo cytotoxicity test using SCID mouse.
Figure 23:
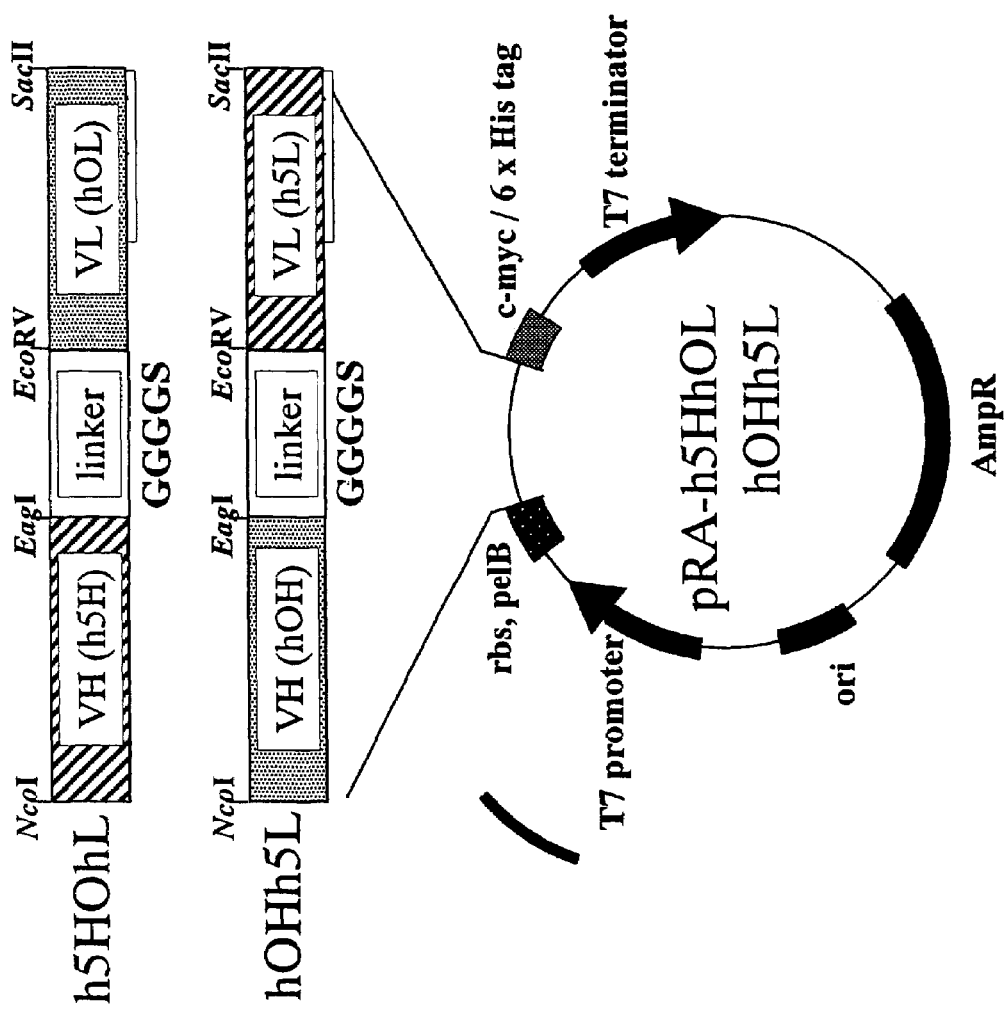
FIG. 23 is a schematic chart showing the structure of hExh3 expression vectors of pRA-h5HhOL and pRA-hOHh5L.

The results clearly showed that while the tumor kept growing in a group administered with T-LAK cells alone and the control group administered with PBS, the growth of the tumor was remarkably inhibited in a group administered with Ex3. Especially, the tumor in a group administered with 20 μg/mouse was degenerated in almost the same degree as in a group administered with chemically-synthesized Ex3 bsAb (FIG. 20).

Example 11

Preparation of Humanized Ex3 Gene

It was already reported that the variable region of the humanized OKT3 could maintain its activity when compared with the mouse OKT3 (Reference 2). The total gene was synthesized by means of overlapping PCR based on the amino acid sequence of the variable regions of the humanized OKT3 disclosed in the Reference 2 (FIG. 21). The optimum codons for E. coli were used in the synthesis. It was also reported that the use of the gene containing the optimum codons would increase the expression level in E. coli.

Reference 2: Adair, J. R. et al. Humanization of the murine anti-human CD3 monoclonal antibody OKT3. Hum Antibodies Hybridomas 5, 41-7. (1994).

The humanization of the variable regions of 528 was performed by means of CDR grafting. Thus, a human antibody having FR (Frame Work) with the highest homology was screened and selected by a homology search in view of the length of each CDR and the like. An amino acid sequence was designed, in which the CDR of the selected human antibody was replaced with CDR of 528. The total gene was then synthesized by means of overlapping PCR by using the optimum codons for E. coli (FIG. 22).

Example 12

Preparation of Expression Vector of Humanized Ex3

The humanized Ex3 diabody (referred to as "hExh3") was made of the two molecules of h5HhOL and hOHh5L. The expression vectors were constructed based on the expression vectors constituting Ex3. Thus, the humanized 5H (referred to as "h5H": SEQ ID No. 29) was amplified with PCR using E-F primers comprising a restriction enzyme site, digested by NcoI-EagI, and replaced with "5H" in pRA-5HOL. Then, the humanized OL (referred to as "hOL": SEQ ID No. 28) was amplified with PCR using G-H primers comprising a restriction enzyme site, digested by EcoRV-SacII, and replaced with "OL" in pRA-5HOL to finally give pRA-h5HhOL. Similarly, the humanized OH (referred to as "hOH": SEQ ID No. 27) was amplified with PCR using I-J primers comprising a restriction enzyme site, digested by NcoI-EagI, and replaced with "OH" in pRA-OH5L. Then, the humanized 5L (referred to as "h5L": SEQ ID No. 30) was amplified with PCR using K-L primers comprising a restriction enzyme site, digested by EcoRV-SacII, and replaced with "5L" in pRA-OH5L to finally give pRA-hOHh5L. As in Ex3, a c-myc peptide tag for detection and a His-tag (Hisx6: histidine-hexamer) for purification were introduced successively in the vectors.

```
E  NcoI-h5H back primer           [SEQ ID No.5]
5'-nnnccatggcccaggtgcaactggttcagagc-3'

F  h5H-EagI forward primer        [SEQ ID No.6]
5'-nnncggccgagctcacggtaaccagcgta-3'

G  EcoRV-hOL back primer          [SEQ ID No.7]
5'-nnngatatccagatgacccagag-3'

H  hOL-SacII forward primer       [SEQ ID No.8]
5'-nnnccgcggcgcgggtaatctgc-3'

I  NcoI-hOH back primer           [SEQ ID No.9]
5'-nnnccatggcccaggtgcaactggtg-3'

J  hOH-EagI forward primer        [SEQ ID No.10]
5'-nnncggccgagctaacggtcacc-3'

K  EcoRV-h5L back primer          [SEQ ID No.11]
5'-nnngatatcgtgatgacccagagccc-3'

L  h5L SacII forward primer       [SEQ ID No.12]
5'-nnnccgcggcgcgtttaatttccactttggtgccac-3'
```

Example 13

Expression in *E. coli*, Purification and Refolding of "h5HhOL" and "hOHh5L"

Figure 24:
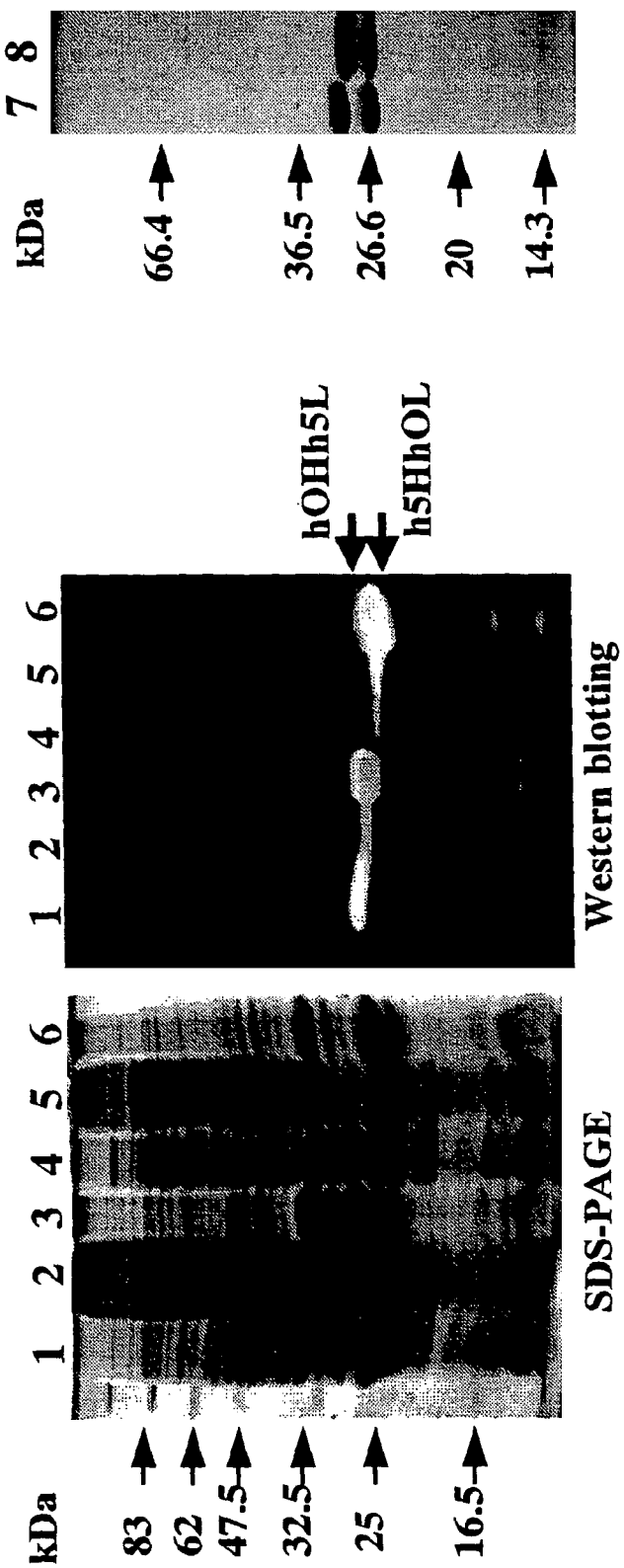
FIG. 24 shows photos of SDS-PAGE (left and Western-blotting (right) showing the expression of h5HhOL and hOHh5L.

*E. coli*. cells transformed with the expression vectors pRA-h5HhOL and pRA-hOHh5L were cultured by the same way as in Example 3. Since SDS-PAGE and Western-blotting of each fraction revealed that almost all of the "h5HhOL" and "hOHh5L" was contained in the insoluble fraction within the bacteria cell, these proteins were prepared from said insoluble fraction (FIG. 24).

Purification and refolding were carried out by the same procedures as in Example 4. After being separately purified, the same quantity of "h5HhOL" and "hOHh5L" was mixed together and refolded. SDS-PAGE of the refolded hExh3 showed that they were purified with a very high degree and they had formed a homogeneous hetero-dimer (FIG. 24, lanes 1 & 4: culture supernatant; lanes 2 & 5: soluble fraction within the bacteria cell; lanes 3 & 6: insoluble fraction within the bacteria cell; lane 7: after purification and refolding of hExh3; lane 8: after purification and refolding of Ex3).

Example 14

Evaluation of hExh3—Flow Cytometric Analysis

Figure 25:
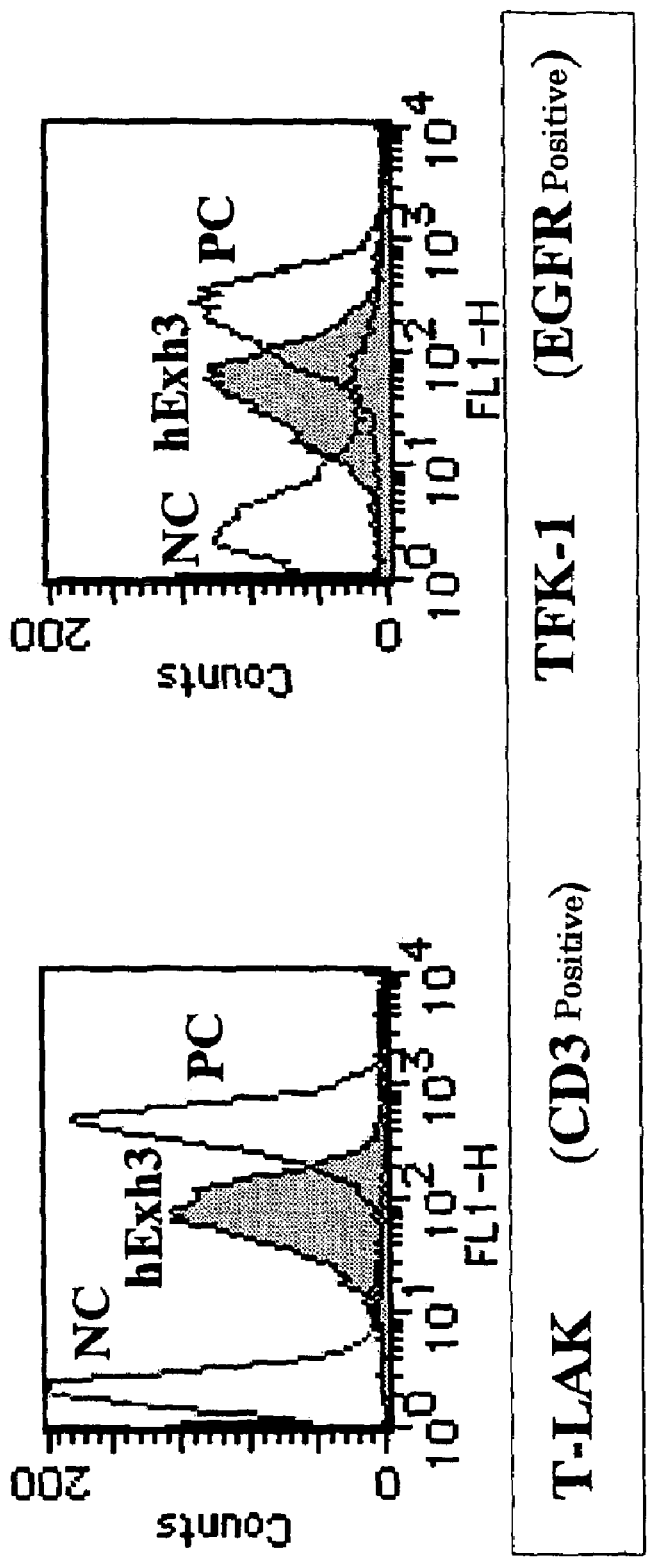
FIG. 25 shows the results of binding activity of hExh3 to various cells by Flow Cytometry.

The binding of hExh3 was examined with Flow cytometry by the same way as in Example 5. The negative control (NC) and positive control (PC) were taken as well in the same way as in Example 5. The results showed its binding to both the T-LAK cell and TFK-1 cell as in Ex3 (FIG. 25).

Example 15

Alternation of the Function of hExh3 Caused by Introduction of Mutation

Alternation of the function of hExh3 caused by introduction of mutation was examined. There has been some reports that the humanization could cause reduction and loss of the function of the antibody itself. It was therefore thought necessary to introduce a site-specific mutation into a part of the sequence that had changed due to the humanization in the FR, which may affect the CDR structure, such as canonical structure (some fixed CDR structure) or vernier residues, so that the changed part will be modified back to that of the original mouse sequence.

The vernier residues are contained in FR and positioned in the vicinity of CDR, which are involved in the formation and adjustment of basis of CDR structure and in the binding to an antigen (Reference 3). However, the vernier residues involved in restoring of the activity are different in each antibody. It is therefore generally selected by actually preparing some mutants and evaluating their biding activities and the like, although it may be predicted to some extent by a detailed structure analysis (Reference 4, 5).

Each site-specific mutation was introduced by means of overlapping PCR. Thus, the PCR-amplified products obtained form h5H with the use of E-N primers and F-M primers were used as templates for $2^{nd}$ PCR, which was done with the use of primers E-F. After the digestion with NcoI-EagI, the $2^{nd}$ PCR product was replaced with h5H of pRA-h5HhOL to give pRA-h5HhOL comprising a mutant M48I of h5H (Ile instead of Met at 48; referred to as "h5H-m01"). Ten mutants were prepared by the similar manner (Table 2, FIG. 26).

TABLE 2

| mutant | $1^{st}$ template | $1^{st}$ primers | | sites of mutation |
|---|---|---|---|---|
| h5H-m01 | h5H | E-N | F-M | M48I, |
| h5H-m02 | h5H-m01 | E-P | F-O | M48I, A93T |
| h5H-m03 | h5H | E-R | F-Q | R66K, R71V |
| h5H-m04 | h5H-m01 | E-R | F-Q | M48I, R66K, R71V |
| h5H-m05 | h5H-m04 | E-T | F-S | Y27D, M48I, R66K, R71V |
| h5H-m06 | h5H-m04 | E-P | F-0 | M48I, R66K, R71V, A93T |
| h5H-m07 | h5H-m03 | E-V | F-U | R66K, M69L, R71V, T73R |
| h5H-m08 | h5H-m07 | E-N | F-M | M48I, R66K, M69L, R71V, T73R |
| h5H-m09 | h5H-m08 | E-P | F-O | M48I, R66K, M69L, R17V, T73R, A93T |
| h5H-m10 | h5H-m04 | E-X | F-W | M48I, R66K, R71V, I75S, S76R, A78V |

```
M h5H -M48I(+)                          [SEQ ID No.13]
  5'-gcctggaatggattggtaacatttatc-3'

N h5H-M48I(-)                           [SEQ ID No.14]
  5'-gataaatgttaccaatccattccaggc-3'

O h5H-A93T(+)                           [SEQ ID No.15]
  5'-tattactgcacgcgcagtggc-3'

P h5H-A93T(-)                           [SEQ ID No.16]
  5'-gccactgcgcgtgcagtaata-3'

Q h5H-R66KR71V(+)                       [SEQ ID No.17]
  5'-atttaagaacaaagtgaccatgacggttgataccagca-3'

R h5H-R66KR71V(-)                       [SEQ ID No.18]
  5'-tgctggtatcaaccgtcatggtcactttgttcttaaat-3'

S h5H-Y27D(+)                           [SEQ ID No.19]
  5'-gcctcaggcgatacctttacg-3'

T h5H-Y27D(-)                           [SEQ ID No.20]
  5'-cgtaaaggtatcgcctgaggc-3'

U h5H-M69LT73R(+)                       [SEQ ID No.21]
  5'-caaagtgaccctgacggttgatcgcagcatttcga-3'

V h5H-M69LT73R(-)                       [SEQ ID No.22]
  5'-tcgaaatgctgcgatcaaccgtcagggtcactttg-3'

W h5H-I75SS76RA78V(+)                   [SEQ ID No.23]
  5'-gataccagcagtcgcacggtctatatggaa-3'

X h5H-I75SS76RA78V(-)                   [SEQ ID No.24]
  5'-ttccatatagaccgtgcgactgctggtatc-3'
```

Reference 3: Foote, J. & Winter, G. Antibody framework residues affecting the conformation of the hypervariable loops. J. Mol. Biol. 224, 487-99. (1992).

Reference 4: Sato, K. et al. Reshaping a human antibody to inhibit the interleukin Reference 5: Sato, K. et al. Humanization of a mouse anti-human interleukin-6 receptor antibody comparing two methods for selecting human framework regions. Mol. Immunol. 31, 371-81. (1994).

Example 16

Evaluation of hExh3 and its Mutants—In Vitro Cytotoxicity Test (MTS Asssay)

Figure 27:
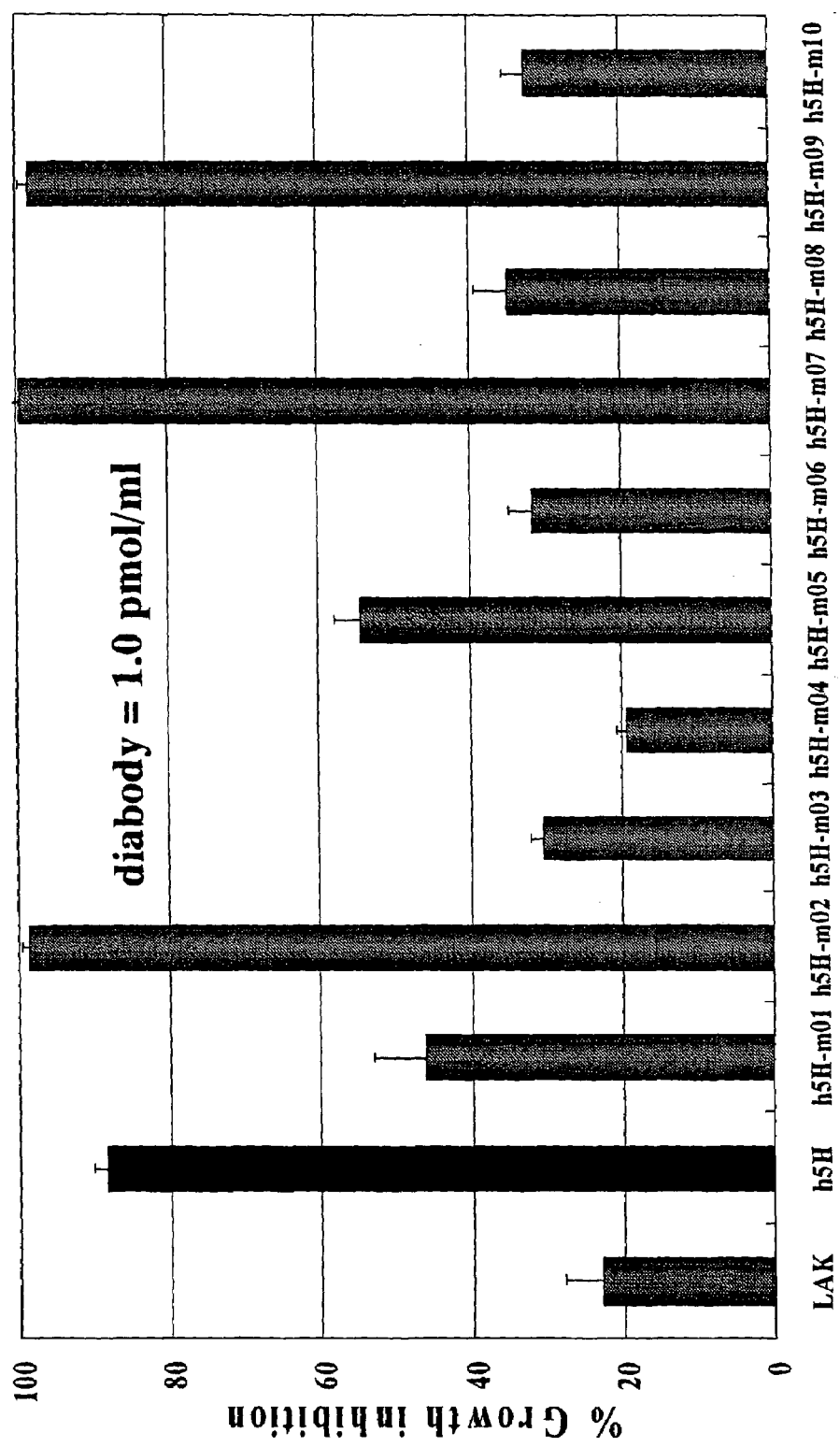
FIG. 27 shows the results of in vitro cytotoxicity test (MTS assay) by hExh3 and its mutants.

The cytotoxicity in vitro of hExh3 and its mutants were evaluated by the MTS assay as in Example 7, revealing that the introduction of mutations at a few sites would significantly affect the cytotoxicity and that some of the mutants showed slightly stronger activity than that of hExh3 (FIG. 27).

Figure 28:
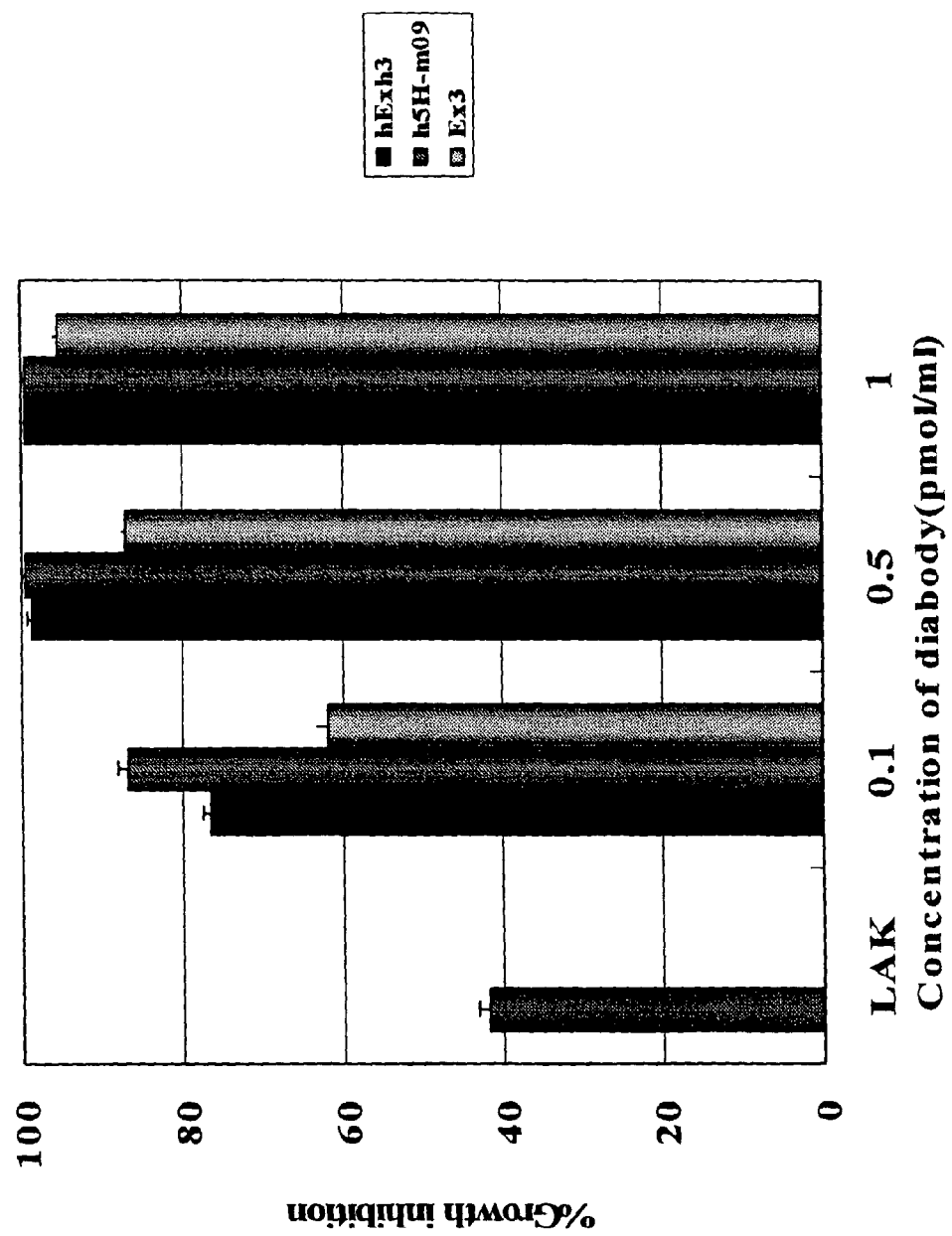
FIG. 28 shows the results in vitro cytotoxicity test (MTS assay) indicating concentration-dependency by hExh3 (left bar), its mutants h5H-m09 (middle bar) and Ex3 (right bar).

The cytotoxicity depending on the concentration was also observed, showing that hExh3 (left bar) and h5H-m09 (middle bar) had the same effect as that of Ex3 (right bar) (FIG. 28).

INDUSTRIAL APPLICABILITY

It was confirmed that the diabody-type bispecific antibody according to the present invention showed an excellent cytotoxicity in vitro and in vivo. Furthermore, the addition of the diabody-type antibody to the culture system comprising the cell having phagocytosis or cytotoxic activity and the cell expressing human epidermal growth factor (EGF) receptor will significantly increase the production of cytokines by the cells having phagocytosis or cytotoxic activity. The humanized diabody-type bispecific antibody was also produced and it was confirmed that it showed the activity comparable to that derived from mouse.

It was confirmed that the diabody-type bispecific antibody according to the present invention could be stored frozen while keeping its activity for a few months, showing its excellent stability.

Accordingly, the pharmaceutical preparation comprising these diabody-type bispecific antibodies as an active ingredient has activities of eliminating, hurting, damaging and/or reducing tumor cells in vitro and in vivo, and is used as an anti-tumor agent.

```

What is claimed:

1. A humanized diabody-type bispecific antibody selected from the group consisting of:
(A) a first single-chain polypeptide comprising
a heavy chain comprising a variable region comprising the amino acid sequence according to SEQ ID NO:43, and a light chain comprising a variable region comprising the amino acid sequence according to SEQ ID NO:46, and
a second single-chain polypeptide comprising
a light chain comprising a variable region comprising the amino acid sequence according to SEQ ID NO:44, and a heavy chain comprising a variable region comprising the amino acid sequence according to SEQ ID NO:45,
B) a first single-chain polypeptide comprising
a heavy chain comprising a variable region comprising the amino acid sequence according to SEQ ID NO:43 and a light chain comprising a variable region comprising the amino acid sequence according to SEQ ID NO:46, and
a second single-chain polypeptide comprising a light chain comprising a variable region comprising the amino acid sequence according to SEQ ID NO:44 and a heavy chain comprising a variable region comprising the amino acid sequence according to SEQ ID NO:45, wherein Met at position 48 and Ala at position 93 of the heavy chain sequence according to SEQ ID NO:45 are replaced by Ile and Thr, respectively,
(C) a first single-chain polypeptide comprising
a heavy chain comprising a variable region comprising the amino acid sequence according to SEQ ID NO:43 and a light chain comprising a variable region comprising the amino acid sequence according to SEQ ID NO:46, and
a second single-chain polypeptide comprising
a light chain comprising a variable region comprising the amino acid sequence according to SEQ ID NO:44 and a heavy chain comprising a variable region comprising the amino acid sequence according to SEQ ID NO:45, wherein Arg at position 66, Met at position 69, Arg at position 71 and Thr at position 73 of the heavy chain sequence according to SEQ ID NO:45 are replaced by Lys, Leu, Val and Arg, respectively, and
(D) a first single-chain polypeptide comprising
a heavy chain comprising a variable region comprising the amino acid sequence according to SEQ ID NO:43 and a light chain comprising a variable region comprising the amino acid sequence according to SEQ ID NO:46, and
a second single-chain polypeptide comprising
a light chain comprising a variable region comprising the amino acid sequence according to SEQ ID NO:44 and a heavy chain comprising a variable region comprising the amino acid sequence according to SEQ ID NO:45, wherein Met at position 48, Arg at position 66, Met at position 69, Arg at position 71, Thr at position 73 and Ala at position 93 of the heavy chain sequence according to SEQ ID NO:45 are replaced by Ile, Lys, Leu, Val, Arg and Thr, respectively.

2. The humanized diabody-type bispecific antibody according to claim 1 which is (A).

3. The humanized diabody-type bispecific antibody according to claim 1 which is (B).

4. The humanized diabody-type bispecific antibody according to claim 1 which is (C).

5. The humanized diabody-type bispecific antibody according to claim 1 which is (D).

6. A method for the production of a diabody-type bispecific antibody, comprising
culturing a host cell transformed with a nucleic acid encoding a first polypeptide of claim 1,
culturing a host cell transformed with a nucleic acid encoding a second polypeptide of claim 1,
expressing the nucleic acids,
collecting the expressed first and second polypeptides,
purifying the first and second polypeptides, and
assembling the first and second polypeptides to form the diabody-type bispecific antibody of claim 1, and
separating and collecting the diabody-type antibody.

7. A pharmaceutical preparation comprising the diabody-type bispecific antibody according to claim 1.

8. The pharmaceutical preparation according to claim 4 for use in increasing the production of cytokines by cells expressing CD3, and having phagocytosis or cytotoxic activity.

9. A method for increasing the production of cytokines by cells expressing CD3, and having phagocytosis or cytotoxic activity, comprising adding the diabody-type bispecific antibody according to claim 1 to a culture system containing the cells expressing CD3, and having phagocytosis or cytotoxic activity, and tumor cells expressing the human EGF receptor, HER-1/ErbB1.

* * * * *

SEQUENCE LISTING

<160> NUMBER OF SEQ ID NOS: 40

<210> SEQ ID NO 1
<211> LENGTH: 33
<212> TYPE: DNA
<213> ORGANISM: Artificial Sequence
<220> FEATURE:
<223> OTHER INFORMATION: A NcoI-5H back primer
<220> FEATURE:
<221> NAME/KEY: misc_feature
<222> LOCATION: (1)..(3)
<223> OTHER INFORMATION: n is a, c, g, or t

<400> SEQUENCE: 1
nnnccatggc ccaggtccag ctgcagcagt ctg                              33

<210> SEQ ID NO 2
<211> LENGTH: 28
<212> TYPE: DNA
<213> ORGANISM: Artificial Sequence
<220> FEATURE:
<223> OTHER INFORMATION: B 5H-EagI forward primer
<220> FEATURE:
<221> NAME/KEY: misc_feature
<222> LOCATION: (1)..(3)
<223> OTHER INFORMATION: n is a, c, g, or t

<400> SEQUENCE: 2
nnncggccga ggagactgtg agagtggt                                    28

<210> SEQ ID NO 3
<211> LENGTH: 26
<212> TYPE: DNA
<213> ORGANISM: Artificial Sequence
<220> FEATURE:
<223> OTHER INFORMATION: C EcoRV-5L back primer
<220> FEATURE:
<221> NAME/KEY: misc_feature
<222> LOCATION: (1)..(3)
<223> OTHER INFORMATION: n is a, c, g, or t

<400> SEQUENCE: 3
nnngatatcc taatgaccca atctcc                                      26

<210> SEQ ID NO 4
<211> LENGTH: 29
<212> TYPE: DNA
<213> ORGANISM: Artificial Sequence
<220> FEATURE:
```

```
<223> OTHER INFORMATION: D 5L-SacII forward primer
<220> FEATURE:
<221> NAME/KEY: misc_feature
<222> LOCATION: (1)..(3)
<223> OTHER INFORMATION: n is a, c, g, or t

<400> SEQUENCE: 4
nnnccgcggc acgtttgatt tccagcttg                                29

<210> SEQ ID NO 5
<211> LENGTH: 32
<212> TYPE: DNA
<213> ORGANISM: Artificial Sequence
<220> FEATURE:
<223> OTHER INFORMATION: E NcoI-h5H back primer
<220> FEATURE:
<221> NAME/KEY: misc_feature
<222> LOCATION: (1)..(3)
<223> OTHER INFORMATION: n is a, c, g, or t

<400> SEQUENCE: 5
nnnccatggc ccaggtgcaa ctggttcaga gc                            32

<210> SEQ ID NO 6
<211> LENGTH: 29
<212> TYPE: DNA
<213> ORGANISM: Artificial Sequence
<220> FEATURE:
<223> OTHER INFORMATION: F h5H-EagI forward primer
<220> FEATURE:
<221> NAME/KEY: misc_feature
<222> LOCATION: (1)..(3)
<223> OTHER INFORMATION: n is a, c, g, or t

<400> SEQUENCE: 6
nnncggccga gctcacggta accagcgta                                29

<210> SEQ ID NO 7
<211> LENGTH: 23
<212> TYPE: DNA
<213> ORGANISM: Artificial Sequence
<220> FEATURE:
<223> OTHER INFORMATION: G EcoRV-hOL back primer
<220> FEATURE:
<221> NAME/KEY: misc_feature
<222> LOCATION: (1)..(3)
<223> OTHER INFORMATION: n is a, c, g, or t

<400> SEQUENCE: 7
nnngatatcc agatgaccca gag                                      23

<210> SEQ ID NO 8
<211> LENGTH: 23
<212> TYPE: DNA
<213> ORGANISM: Artificial Sequence
<220> FEATURE:
<223> OTHER INFORMATION: H hOL-SacII forward primer
<220> FEATURE:
<221> NAME/KEY: misc_feature
<222> LOCATION: (1)..(3)
<223> OTHER INFORMATION: n is a, c, g, or t

<400> SEQUENCE: 8
nnnccgcggc gcgggtaatc tgc                                      23

<210> SEQ ID NO 9
<211> LENGTH: 26
<212> TYPE: DNA
<213> ORGANISM: Artificial Sequence
```

```
<220> FEATURE:
<223> OTHER INFORMATION: I NcoI-hOH back primer
<220> FEATURE:
<221> NAME/KEY: misc_feature
<222> LOCATION: (1)..(3)
<223> OTHER INFORMATION: n is a, c, g, or t

<400> SEQUENCE: 9
nnnccatggc ccaggtgcaa ctggtg                                              26

<210> SEQ ID NO 10
<211> LENGTH: 23
<212> TYPE: DNA
<213> ORGANISM: Artificial Sequence
<220> FEATURE:
<223> OTHER INFORMATION: J hOH-EagI forward primer
<220> FEATURE:
<221> NAME/KEY: misc_feature
<222> LOCATION: (1)..(3)
<223> OTHER INFORMATION: n is a, c, g, or t

<400> SEQUENCE: 10
nnncggccga gctaacggtc acc                                                 23

<210> SEQ ID NO 11
<211> LENGTH: 26
<212> TYPE: DNA
<213> ORGANISM: Artificial Sequence
<220> FEATURE:
<223> OTHER INFORMATION: K EcoRV-h5L back primer
<220> FEATURE:
<221> NAME/KEY: misc_feature
<222> LOCATION: (1)..(3)
<223> OTHER INFORMATION: n is a, c, g, or t

<400> SEQUENCE: 11
nnngatatcg tgatgaccca gagccc                                              26

<210> SEQ ID NO 12
<211> LENGTH: 36
<212> TYPE: DNA
<213> ORGANISM: Artificial Sequence
<220> FEATURE:
<223> OTHER INFORMATION: L h5L-SacII forward primer
<220> FEATURE:
<221> NAME/KEY: misc_feature
<222> LOCATION: (1)..(3)
<223> OTHER INFORMATION: n is a, c, g, or t

<400> SEQUENCE: 12
nnnccgcggc gcgtttaatt tccactttgg tgccac                                   36

<210> SEQ ID NO 13
<211> LENGTH: 27
<212> TYPE: DNA
<213> ORGANISM: Artificial Sequence
<220> FEATURE:
<223> OTHER INFORMATION: M h5H-M48I(+)

<400> SEQUENCE: 13
gcctggaatg gattggtaac atttatc                                             27

<210> SEQ ID NO 14
<211> LENGTH: 27
<212> TYPE: DNA
<213> ORGANISM: Artificial Sequence
<220> FEATURE:
<223> OTHER INFORMATION: N h5H-M48I(-)
```

```
<400> SEQUENCE: 14
gataaatgtt accaatccat tccaggc                                              27

<210> SEQ ID NO 15
<211> LENGTH: 21
<212> TYPE: DNA
<213> ORGANISM: Artificial Sequence
<220> FEATURE:
<223> OTHER INFORMATION: O h5H-A93T(+)

<400> SEQUENCE: 15
tattactgca cgcgcagtgg c                                                    21

<210> SEQ ID NO 16
<211> LENGTH: 21
<212> TYPE: DNA
<213> ORGANISM: Artificial Sequence
<220> FEATURE:
<223> OTHER INFORMATION: P h5H-A93T(-)

<400> SEQUENCE: 16
gccactgcgc gtgcagtaat a                                                    21

<210> SEQ ID NO 17
<211> LENGTH: 38
<212> TYPE: DNA
<213> ORGANISM: Artificial Sequence
<220> FEATURE:
<223> OTHER INFORMATION: Q h5H-R66KR71V(+)

<400> SEQUENCE: 17
atttaagaac aaagtgacca tgacggttga taccagca                                  38

<210> SEQ ID NO 18
<211> LENGTH: 38
<212> TYPE: DNA
<213> ORGANISM: Artificial Sequence
<220> FEATURE:
<223> OTHER INFORMATION: R h5H-R66KR71V(-)

<400> SEQUENCE: 18
tgctggtatc aaccgtcatg gtcactttgt tcttaaat                                  38

<210> SEQ ID NO 19
<211> LENGTH: 21
<212> TYPE: DNA
<213> ORGANISM: Artificial Sequence
<220> FEATURE:
<223> OTHER INFORMATION: S h5H-Y27D(+)

<400> SEQUENCE: 19
gcctcaggcg ataccttTac g                                                    21

<210> SEQ ID NO 20
<211> LENGTH: 21
<212> TYPE: DNA
<213> ORGANISM: Artificial Sequence
<220> FEATURE:
<223> OTHER INFORMATION: T h5H-Y27D(-)

<400> SEQUENCE: 20
cgtaaaggta tcgcctgagg c                                                    21

<210> SEQ ID NO 21
<211> LENGTH: 35
```

<210> SEQ ID NO 21
<211> LENGTH: 35
<212> TYPE: DNA
<213> ORGANISM: Artificial Sequence
<220> FEATURE:
<223> OTHER INFORMATION: U h5H-M69LT73R(+)

<400> SEQUENCE: 21
caaagtgacc ctgacggttg atcgcagcat ttcga         35

<210> SEQ ID NO 22
<211> LENGTH: 35
<212> TYPE: DNA
<213> ORGANISM: Artificial Sequence
<220> FEATURE:
<223> OTHER INFORMATION: V h5H-M69LT73R(-)

<400> SEQUENCE: 22
tcgaaatgct gcgatcaacc gtcagggtca ctttg         35

<210> SEQ ID NO 23
<211> LENGTH: 30
<212> TYPE: DNA
<213> ORGANISM: Artificial Sequence
<220> FEATURE:
<223> OTHER INFORMATION: W h5H-I75SS76RA78V(+)

<400> SEQUENCE: 23
gataccagca gtcgcacggt ctatatggaa              30

<210> SEQ ID NO 24
<211> LENGTH: 30
<212> TYPE: DNA
<213> ORGANISM: Artificial Sequence
<220> FEATURE:
<223> OTHER INFORMATION: X h5H-I75SS76RA78V(-)

<400> SEQUENCE: 24
ttccatatag accgtgcgac tgctggtatc              30

<210> SEQ ID NO 25
<211> LENGTH: 354
<212> TYPE: DNA
<213> ORGANISM: Mouse
<220> FEATURE:
<221> NAME/KEY: CDS
<222> LOCATION: (1)..(354)
<223> OTHER INFORMATION: 5H

<400> SEQUENCE: 25

```
cag gtc cag ctg cag cag tct ggg tct gag atg gcg agg cct gga gct    48
Gln Val Gln Leu Gln Gln Ser Gly Ser Glu Met Ala Arg Pro Gly Ala
1               5                   10                  15 tca gtg aag ctg ccc tgc aag gct tct ggc gac aca ttc acc agt tac    96
Ser Val Lys Leu Pro Cys Lys Ala Ser Gly Asp Thr Phe Thr Ser Tyr
            20                  25                  30 tgg atg cac tgg gtg aag cag agg cat gga cat ggc cct gag tgg atc   144
Trp Met His Trp Val Lys Gln Arg His Gly His Gly Pro Glu Trp Ile
        35                  40                  45 gga aat att tat cca ggt agt ggt ggt act aac tac gct gag aag ttc   192
Gly Asn Ile Tyr Pro Gly Ser Gly Gly Thr Asn Tyr Ala Glu Lys Phe
    50                  55                  60 aag aac aag gtc act ctg act gta gac agg tcc tcc cgc aca gtc tac   240
Lys Asn Lys Val Thr Leu Thr Val Asp Arg Ser Ser Arg Thr Val Tyr
65                  70                  75                  80 atg cac ctc agc agg ctg aca tct gag gac tct gcg gtc tat tat tgt   288
Met His Leu Ser Arg Leu Thr Ser Glu Asp Ser Ala Val Tyr Tyr Cys
```

```
                        85                  90                  95
aca aga tcg ggg ggt ccc tac ttc ttt gac tac tgg ggc caa ggc acc    336
Thr Arg Ser Gly Gly Pro Tyr Phe Phe Asp Tyr Trp Gly Gln Gly Thr
                100                 105                 110 act ctc aca gtc tcc tcc                                            354
Thr Leu Thr Val Ser Ser
        115

<210> SEQ ID NO 26
<211> LENGTH: 342
<212> TYPE: DNA
<213> ORGANISM: Mouse
<220> FEATURE:
<221> NAME/KEY: CDS
<222> LOCATION: (1)..(342)
<223> OTHER INFORMATION: 5L

<400> SEQUENCE: 26 gac att cta atg acc caa tct cca ctc tcc ctg cct gtc agt ctt gga     48
Asp Ile Leu Met Thr Gln Ser Pro Leu Ser Leu Pro Val Ser Leu Gly
1               5                   10                  15 gat caa gcc tcc atc tct tgc aga tct agt cag aac att gta cat aat     96
Asp Gln Ala Ser Ile Ser Cys Arg Ser Ser Gln Asn Ile Val His Asn
            20                  25                  30 aat gga atc acc tat tta gaa tgg tac ctg caa agg cca ggc cag tct    144
Asn Gly Ile Thr Tyr Leu Glu Trp Tyr Leu Gln Arg Pro Gly Gln Ser
        35                  40                  45 cca aag ctc ctg atc tac aaa gtt tcc gac cga ttt tct ggg gtc cca    192
Pro Lys Leu Leu Ile Tyr Lys Val Ser Asp Arg Phe Ser Gly Val Pro
    50                  55                  60 gac agg ttc agt ggc agt gga tca ggg aca gat ttc aca ctc aag atc    240
Asp Arg Phe Ser Gly Ser Gly Ser Gly Thr Asp Phe Thr Leu Lys Ile
65                  70                  75                  80 agc aga gta gag gct gag gat ctg gga att tat tac tgc ttt caa ggt    288
Ser Arg Val Glu Ala Glu Asp Leu Gly Ile Tyr Tyr Cys Phe Gln Gly
                85                  90                  95 tca cat att cct ccc acg ttc gga ggg ggg acc aag ctg gaa atc aaa    336
Ser His Ile Pro Pro Thr Phe Gly Gly Gly Thr Lys Leu Glu Ile Lys
                100                 105                 110 cgt gcg                                                            342
Arg Ala

<210> SEQ ID NO 27
<211> LENGTH: 357
<212> TYPE: DNA
<213> ORGANISM: Artificial Sequence
<220> FEATURE:
<221> NAME/KEY: CDS
<222> LOCATION: (1)..(357)
<223> OTHER INFORMATION: Chimeric Sequence (hOH)

<400> SEQUENCE: 27 cag gtg caa ctg gtg cag agc ggc ggt ggc gtt gtg cag ccg ggc cgc     48
Gln Val Gln Leu Val Gln Ser Gly Gly Gly Val Val Gln Pro Gly Arg
1               5                   10                  15 agc ctg cgc ctg tct tgc aaa gcg agc ggc tat acc ttt acg cgc tat     96
Ser Leu Arg Leu Ser Cys Lys Ala Ser Gly Tyr Thr Phe Thr Arg Tyr
            20                  25                  30 acc atg cat tgg gtg cgc cag gcg ccg ggc aaa ggt ctg gaa tgg att    144
Thr Met His Trp Val Arg Gln Ala Pro Gly Lys Gly Leu Glu Trp Ile
        35                  40                  45 ggc tat att aac ccg tct cgc ggc tat acc aac tat aat cag aaa gtg    192
Gly Tyr Ile Asn Pro Ser Arg Gly Tyr Thr Asn Tyr Asn Gln Lys Val
```

```
aaa gat cgc ttt acc att agc cgc gat aac tct aaa aac acc gcg ttt      240
Lys Asp Arg Phe Thr Ile Ser Arg Asp Asn Ser Lys Asn Thr Ala Phe
 65                  70                  75                  80 ctg cag atg gat agc ctg cgc ccg gaa gat acc ggc gtg tat ttt tgc      288
Leu Gln Met Asp Ser Leu Arg Pro Glu Asp Thr Gly Val Tyr Phe Cys
                 85                  90                  95 gcg cgc tac tat gat gac cat tat agc ctg gat tat tgg ggc cag ggc      336
Ala Arg Tyr Tyr Asp Asp His Tyr Ser Leu Asp Tyr Trp Gly Gln Gly
            100                 105                 110 acc ccg gtg acc gtt agc tcg                                          357
Thr Pro Val Thr Val Ser Ser
            115
```

<210> SEQ ID NO 28
<211> LENGTH: 324
<212> TYPE: DNA
<213> ORGANISM: Artificial Sequence
<220> FEATURE:
<221> NAME/KEY: CDS
<222> LOCATION: (1)..(324)
<223> OTHER INFORMATION: Chimeric Sequence (hOL)

<400> SEQUENCE: 28

```
gat atc cag atg acc cag agc ccg agc tct ctg agc gcg agc gtg ggc       48
Asp Ile Gln Met Thr Gln Ser Pro Ser Ser Leu Ser Ala Ser Val Gly
 1               5                  10                  15 gat cgc gtg acc att acg tgc agc gcg tct agc tct gtg agc tat atg       96
Asp Arg Val Thr Ile Thr Cys Ser Ala Ser Ser Ser Val Ser Tyr Met
                 20                  25                  30 aac tgg tac cag caa acc cca ggc aaa gcg ccg aaa cgc tgg att tat      144
Asn Trp Tyr Gln Gln Thr Pro Gly Lys Ala Pro Lys Arg Trp Ile Tyr
             35                  40                  45 gat acc agc aaa ctg gcg agc ggc gtg ccg agc cgc ttt agc ggc tct      192
Asp Thr Ser Lys Leu Ala Ser Gly Val Pro Ser Arg Phe Ser Gly Ser
         50                  55                  60 ggt agc ggc acc gat tat acg ttt acc att agc tct ctg cag ccg gaa      240
Gly Ser Gly Thr Asp Tyr Thr Phe Thr Ile Ser Ser Leu Gln Pro Glu
 65                  70                  75                  80 gat att gcg acc tat tac tgc cag caa tgg agc tct aac ccg ttt acc      288
Asp Ile Ala Thr Tyr Tyr Cys Gln Gln Trp Ser Ser Asn Pro Phe Thr
                 85                  90                  95 ttt ggc cag ggt acc aaa ctg cag att acc cgc gcg                      324
Phe Gly Gln Gly Thr Lys Leu Gln Ile Thr Arg Ala
            100                 105
```

<210> SEQ ID NO 29
<211> LENGTH: 354
<212> TYPE: DNA
<213> ORGANISM: Artificial Sequence
<220> FEATURE:
<221> NAME/KEY: CDS
<222> LOCATION: (1)..(354)
<223> OTHER INFORMATION: Chimeric Sequence (h5H)

<400> SEQUENCE: 29

```
cag gtg caa ctg gtt cag agc ggc gcg gaa gtg aaa aag ccg ggc gcg       48
Gln Val Gln Leu Val Gln Ser Gly Ala Glu Val Lys Lys Pro Gly Ala
 1               5                  10                  15 tcg gtt aaa gtg agc tgc aaa gcc tca ggc tat acc ttt acg agc tac       96
Ser Val Lys Val Ser Cys Lys Ala Ser Gly Tyr Thr Phe Thr Ser Tyr
                 20                  25                  30 tgg atg cat tgg gtg cgc cag gcc ccg ggt cag ggc ctg gaa tgg atg      144
```

```
Trp Met His Trp Val Arg Gln Ala Pro Gly Gln Gly Leu Glu Trp Met
        35                  40                  45 ggt aac att tat ccg ggc agc ggt ggc acc aac tat gcg gaa aaa ttt      192
Gly Asn Ile Tyr Pro Gly Ser Gly Gly Thr Asn Tyr Ala Glu Lys Phe
 50                  55                  60 aag aac cgc gtg acc atg acg cgt gat acc agc att tcg acg gcc tat      240
Lys Asn Arg Val Thr Met Thr Arg Asp Thr Ser Ile Ser Thr Ala Tyr
 65                  70                  75                  80 atg gaa ctg agc cgc ctg cgt agc gat gac acc gcc gtg tat tac tgc      288
Met Glu Leu Ser Arg Leu Arg Ser Asp Asp Thr Ala Val Tyr Tyr Cys
                 85                  90                  95 gcg cgc agt ggc ggt ccg tat ttt ttc gat tac tgg ggc cag ggt acg      336
Ala Arg Ser Gly Gly Pro Tyr Phe Phe Asp Tyr Trp Gly Gln Gly Thr
                100                 105                 110 ctg gtt acc gtg agc tcg                                              354
Leu Val Thr Val Ser Ser
        115
```

<210> SEQ ID NO 30
<211> LENGTH: 342
<212> TYPE: DNA
<213> ORGANISM: Artificial Sequence
<220> FEATURE:
<221> NAME/KEY: CDS
<222> LOCATION: (1)..(342)
<223> OTHER INFORMATION: Chimeric Sequence (h5L)

<400> SEQUENCE: 30

```
gat att gtg atg acc cag agc ccg ctg agc ctg ccg gtg acc cca ggc       48
Asp Ile Val Met Thr Gln Ser Pro Leu Ser Leu Pro Val Thr Pro Gly
  1               5                  10                  15 gaa ccg gcg tcg att agc tgc cgc agc tcg cag aac atc gtg cat aat       96
Glu Pro Ala Ser Ile Ser Cys Arg Ser Ser Gln Asn Ile Val His Asn
                 20                  25                  30 aac ggc att acc tat ctg gaa tgg tat ctg cag aaa ccg ggc caa agc      144
Asn Gly Ile Thr Tyr Leu Glu Trp Tyr Leu Gln Lys Pro Gly Gln Ser
         35                  40                  45 ccg cag ctg tta att tat aaa gtg agc gat cgc ttt agc ggc gtg ccg      192
Pro Gln Leu Leu Ile Tyr Lys Val Ser Asp Arg Phe Ser Gly Val Pro
     50                  55                  60 gat cgc ttt tcg ggc agc ggt agt ggc acc gat ttt acg ctg aaa att      240
Asp Arg Phe Ser Gly Ser Gly Ser Gly Thr Asp Phe Thr Leu Lys Ile
 65                  70                  75                  80 agc cgc gtg gaa gcg gag gat gtt ggc gtg tat tac tgc ttt cag ggc      288
Ser Arg Val Glu Ala Glu Asp Val Gly Val Tyr Tyr Cys Phe Gln Gly
                 85                  90                  95 agc cat atc ccg cca acc ttt ggc caa ggc acc aaa gtg gaa att aaa      336
Ser His Ile Pro Pro Thr Phe Gly Gln Gly Thr Lys Val Glu Ile Lys
                100                 105                 110 cgc gcg                                                              342
Arg Ala
```

<210> SEQ ID NO 31
<211> LENGTH: 118
<212> TYPE: PRT
<213> ORGANISM: Artificial Sequence
<220> FEATURE:
<223> OTHER INFORMATION: Chimeric Sequence (h5H-m01)

<400> SEQUENCE: 31

```
Gln Val Gln Leu Val Gln Ser Gly Ala Glu Val Lys Lys Pro Gly Ala
  1               5                  10                  15
```

```
Ser Val Lys Val Ser Cys Lys Ala Ser Gly Tyr Thr Phe Thr Ser Tyr
         20                  25                  30

Trp Met His Trp Val Arg Gln Ala Pro Gly Gln Gly Leu Glu Trp Ile
         35                  40                  45

Gly Asn Ile Tyr Pro Gly Ser Gly Gly Thr Asn Tyr Ala Glu Lys Phe
     50                  55                  60

Lys Asn Arg Val Thr Met Thr Arg Asp Thr Ser Ile Ser Thr Ala Tyr
65                   70                  75                  80

Met Glu Leu Ser Arg Leu Arg Ser Asp Asp Thr Ala Val Tyr Tyr Cys
                 85                  90                  95

Ala Arg Ser Gly Gly Pro Tyr Phe Phe Asp Tyr Trp Gly Gln Gly Thr
             100                 105                 110

Leu Val Thr Val Ser Ser
             115

<210> SEQ ID NO 32
<211> LENGTH: 118
<212> TYPE: PRT
<213> ORGANISM: Artificial Sequence
<220> FEATURE:
<223> OTHER INFORMATION: Chimeric Sequence (h5H-m02)

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
         20                  25                  30

Trp Met His Trp Val Arg Gln Ala Pro Gly Gln Gly Leu Glu Trp Ile
         35                  40                  45

Gly Asn Ile Tyr Pro Gly Ser Gly Gly Thr Asn Tyr Ala Glu Lys Phe
     50                  55                  60

Lys Asn Arg Val Thr Met Thr Arg Asp Thr Ser Ile Ser Thr Ala Tyr
65                   70                  75                  80

Met Glu Leu Ser Arg Leu Arg Ser Asp Asp Thr Ala Val Tyr Tyr Thr
                 85                  90                  95

Ala Arg Ser Gly Gly Pro Tyr Phe Phe Asp Tyr Trp Gly Gln Gly Thr
             100                 105                 110

Leu Val Thr Val Ser Ser
             115

<210> SEQ ID NO 33
<211> LENGTH: 118
<212> TYPE: PRT
<213> ORGANISM: Artificial Sequence
<220> FEATURE:
<223> OTHER INFORMATION: Chimeric Sequence (h5H-m03)

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
         20                  25                  30

Trp Met His Trp Val Arg Gln Ala Pro Gly Gln Gly Leu Glu Trp Met
         35                  40                  45

Gly Asn Ile Tyr Pro Gly Ser Gly Gly Thr Asn Tyr Ala Glu Lys Phe
     50                  55                  60

Lys Asn Lys Val Thr Met Thr Val Asp Thr Ser Ile Ser Thr Ala Tyr
65                   70                  75                  80
```

Met Glu Leu Ser Arg Leu Arg Ser Asp Asp Thr Ala Val Tyr Tyr Cys
                85                  90                  95

Ala Arg Ser Gly Gly Pro Tyr Phe Phe Asp Tyr Trp Gly Gln Gly Thr
            100                 105                 110

Leu Val Thr Val Ser Ser
        115

<210> SEQ ID NO 34
<211> LENGTH: 118
<212> TYPE: PRT
<213> ORGANISM: Artificial Sequence
<220> FEATURE:
<223> OTHER INFORMATION: Chimeric Sequence (h5H-m04)

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Asn Ile Tyr Pro Gly Ser Gly Gly Thr Asn Tyr Ala Glu Lys Phe
    50                  55                  60

Lys Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Gly Pro Tyr Phe Phe Asp Tyr Trp Gly Gln Gly Thr
            100                 105                 110

Leu Val Thr Val Ser Ser
        115

<210> SEQ ID NO 35
<211> LENGTH: 118
<212> TYPE: PRT
<213> ORGANISM: Artificial Sequence
<220> FEATURE:
<223> OTHER INFORMATION: Chimeric Sequence (h5H-m05)

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Phe Thr Ser Tyr
            20                  25                  30

Trp Met His Trp Val Arg Gln Ala Pro Gly Gln Gly Leu Glu Trp Ile
        35                  40                  45

Gly Asn Ile Tyr Pro Gly Ser Gly Gly Thr Asn Tyr Ala Glu Lys Phe
    50                  55                  60

Lys Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Gly Pro Tyr Phe Phe Asp Tyr Trp Gly Gln Gly Thr
            100                 105                 110

Leu Val Thr Val Ser Ser
        115

```
<210> SEQ ID NO 36
<211> LENGTH: 118
<212> TYPE: PRT
<213> ORGANISM: Artificial Sequence
<220> FEATURE:
<223> OTHER INFORMATION: Chimeric Sequence (h5H-m06)

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Ile
            35                  40                  45

Gly Asn Ile Tyr Pro Gly Ser Gly Gly Thr Asn Tyr Ala Glu Lys Phe
        50                  55                  60

Lys Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Thr
                85                  90                  95

Ala Arg Ser Gly Gly Pro Tyr Phe Phe Asp Tyr Trp Gly Gln Gly Thr
            100                 105                 110

Leu Val Thr Val Ser Ser
        115

<210> SEQ ID NO 37
<211> LENGTH: 118
<212> TYPE: PRT
<213> ORGANISM: Artificial Sequence
<220> FEATURE:
<223> OTHER INFORMATION: Chimeric Sequence (h5H-m07)

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Asn Ile Tyr Pro Gly Ser Gly Gly Thr Asn Tyr Ala Glu Lys Phe
        50                  55                  60

Lys Asn Lys Val Thr Leu Thr Val Asp Arg Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Gly Pro Tyr Phe Phe Asp Tyr Trp Gly Gln Gly Thr
            100                 105                 110

Leu Val Thr Val Ser Ser
        115

<210> SEQ ID NO 38
<211> LENGTH: 118
<212> TYPE: PRT
<213> ORGANISM: Artificial Sequence
<220> FEATURE:
<223> OTHER INFORMATION: Chimeric Sequence (h5H-m08)

<400> SEQUENCE: 38

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
            35                  40                  45

Gly Asn Ile Tyr Pro Gly Ser Gly Gly Thr Asn Tyr Ala Glu Lys Phe
        50                  55                  60

Lys Asn Lys Val Thr Leu Thr Val Asp Arg Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Gly Pro Tyr Phe Phe Asp Tyr Trp Gly Gln Gly Thr
            100                 105                 110

Leu Val Thr Val Ser Ser
        115

<210> SEQ ID NO 39
<211> LENGTH: 118
<212> TYPE: PRT
<213> ORGANISM: Artificial Sequence
<220> FEATURE:
<223> OTHER INFORMATION: Chimeric Sequence (h5H-m09)

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
            35                  40                  45

Gly Asn Ile Tyr Pro Gly Ser Gly Gly Thr Asn Tyr Ala Glu Lys Phe
        50                  55                  60

Lys Asn Lys Val Thr Leu Thr Val Asp Arg Ser Ile Ser Thr Ala Tyr
65                  70                  75                  80

Met Glu Leu Ser Arg Leu Arg Ser Asp Asp Thr Ala Val Tyr Tyr Thr
                85                  90                  95

Ala Arg Ser Gly Gly Pro Tyr Phe Phe Asp Tyr Trp Gly Gln Gly Thr
            100                 105                 110

Leu Val Thr Val Ser Ser
        115

<210> SEQ ID NO 40
<211> LENGTH: 118
<212> TYPE: PRT
<213> ORGANISM: Artificial Sequence
<220> FEATURE:
<223> OTHER INFORMATION: Chimeric Sequence (h5H-m10)

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
            35                  40                  45

Gly Asn Ile Tyr Pro Gly Ser Gly Gly Thr Asn Tyr Ala Glu Lys Phe
        50                  55                  60

Lys Asn Lys Val Thr Met Thr Val Asp Thr Ser Ser Arg Thr Val Tyr

-continued

```
                65                  70                  75                  80
            Met Glu Leu Ser Arg Leu Arg Ser Asp Asp Thr Ala Val Tyr Tyr Thr
                            85                  90                  95

Ala Arg Ser Gly Gly Pro Tyr Phe Phe Asp Tyr Trp Gly Gln Gly Thr
                        100                 105                 110

Leu Val Thr Val Ser Ser
                        115
```